(12) United States Patent
Cheng et al.

(10) Patent No.: US 12,042,423 B2
(45) Date of Patent: Jul. 23, 2024

(54) FLUID COLLECTION SYSTEMS INCLUDING AT LEAST ONE TENSIONING ELEMENT

(71) Applicant: PureWick Corporation, El Cajon, CA (US)

(72) Inventors: Jason Jishen Cheng, Covington, GA (US); Eric Rehm, Greensboro, GA (US); Nicholas Austerman, Atlanta, GA (US)

(73) Assignee: PureWick Corporation, Covington, GA (US)

( * ) Notice: Subject to any disclaimer, the term of this patent is extended or adjusted under 35 U.S.C. 154(b) by 70 days.

(21) Appl. No.: 17/448,811

(22) Filed: Sep. 24, 2021

(65) Prior Publication Data

US 2022/0104964 A1 Apr. 7, 2022

Related U.S. Application Data

(60) Provisional application No. 63/088,511, filed on Oct. 7, 2020.

(51) Int. Cl.
*A61F 5/455* (2006.01)
*A61F 5/44* (2006.01)

(52) U.S. Cl.
CPC ............ *A61F 5/455* (2013.01); *A61F 5/4404* (2013.01)

(58) Field of Classification Search
CPC ......... A61F 5/455; A61F 5/4404; A61F 5/453
See application file for complete search history.

(56) References Cited

U.S. PATENT DOCUMENTS

| 737,443 A | 8/1903 | Mooers |
| 1,032,841 A | 7/1912 | Koenig |

(Continued)

FOREIGN PATENT DOCUMENTS

| AU | 2018216821 A1 | 8/2019 |
| AU | 2021299304 A1 | 2/2023 |

(Continued)

OTHER PUBLICATIONS

US 9,908,683 B2, 03/2018, Sandhausen et al. (withdrawn)

(Continued)

*Primary Examiner* — Leslie A Lopez
*Assistant Examiner* — Katherine-Ph Minh Pham
(74) *Attorney, Agent, or Firm* — Dorsey & Whitney

(57) ABSTRACT

Embodiments disclosed herein are directed to fluid collection systems and methods of using the same. An example fluid collection system includes a fluid collection assembly and at least one tensioning element (e.g., wire). The fluid collection assembly includes a fluid impermeable barrier that defines at least a chamber and at least one porous material disposed in the chamber. The tensioning element of the fluid collection system is configured to switch from a relaxed state and a tensioned state. The tensioning element is in the relaxed state when substantially no external tensile force is applied thereto and the tensioned state when an external tensile force is applied thereto. The tensioning element is configured to change a curvature of at least a portion of the fluid collection assembly, for example, by switching the tensioning element between the relaxed state and the tensioned state.

20 Claims, 6 Drawing Sheets

(56) References Cited

U.S. PATENT DOCUMENTS

| | | |
|---|---|---|
| 1,178,644 A | 4/1916 | Johnson |
| 1,742,080 A | 12/1929 | Jones |
| 1,979,899 A | 11/1934 | Obrien et al. |
| 2,241,010 A | 5/1941 | Chipley |
| 2,262,772 A | 11/1941 | Peder |
| 2,326,881 A | 8/1943 | Packer |
| 2,379,346 A | 6/1945 | Farrell |
| 2,485,555 A | 10/1949 | Bester |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A | 1/1961 | Duke |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,171,506 A | 3/1965 | Therkel |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | Mcguire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,683,918 A | 8/1972 | Pizzella |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,881,486 A | 5/1975 | Fenton |
| 3,881,489 A | 5/1975 | Hartwell |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,064,962 A | 12/1977 | Hunt |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,203,503 A | 5/1980 | Bertotti et al. |
| 4,209,076 A | 6/1980 | Bertotti et al. |
| 4,233,025 A | 11/1980 | Larson et al. |
| 4,233,978 A | 11/1980 | Hickey |
| 4,246,901 A | 1/1981 | Frosch et al. |
| 4,253,542 A | 3/1981 | Ruspa et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,330,239 A | 5/1982 | Gannaway |
| 4,352,356 A | 10/1982 | Tong |
| 4,360,933 A | 11/1982 | Kimura et al. |
| 4,365,363 A | 12/1982 | Windauer |
| 4,375,841 A | 3/1983 | Vielbig |
| 4,387,726 A | 6/1983 | Denard |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,551,141 A | 11/1985 | McNeil |
| 4,553,968 A | 11/1985 | Komis |
| 4,581,026 A | 4/1986 | Schneider |
| 4,589,516 A | 5/1986 | Inoue et al. |
| 4,601,716 A | 7/1986 | Smith |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,655,754 A | 4/1987 | Richmond et al. |
| 4,656,675 A | 4/1987 | Fajnsztajn |
| 4,681,570 A | 7/1987 | Dalton |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,735,841 A | 4/1988 | Sourdet |
| 4,743,236 A | 5/1988 | Manschot |
| 4,747,166 A | 5/1988 | Kuntz |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |
| 4,813,943 A | 3/1989 | Smith |
| 4,820,297 A | 4/1989 | Kaufman et al. |
| 4,846,818 A | 7/1989 | Keldahl et al. |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart |
| 4,883,465 A | 11/1989 | Brennan |
| 4,886,498 A | 12/1989 | Newton |
| 4,886,508 A | 12/1989 | Washington |
| 4,886,509 A | 12/1989 | Mattsson |
| 4,889,532 A | 12/1989 | Metz et al. |
| 4,889,533 A | 12/1989 | Beecher |
| 4,890,691 A | 1/1990 | Ching-Ho |
| 4,903,254 A | 2/1990 | Haas |
| 4,904,248 A | 2/1990 | Vaillancourt |
| 4,905,692 A | 3/1990 | More |
| 4,936,838 S | 6/1990 | Cross et al. |
| 4,955,922 A | 9/1990 | Terauchi |
| 4,957,487 A | 9/1990 | Gerow |
| 4,965,460 A | 10/1990 | Tanaka et al. |
| 4,987,849 A | 1/1991 | Sherman |
| 5,002,541 A | 3/1991 | Conkling et al. |
| 5,004,463 A | 4/1991 | Nigay |
| 5,031,248 A | 7/1991 | Kemper |
| 5,045,077 A | 9/1991 | Blake |
| 5,045,283 A | 9/1991 | Patel |
| 5,049,144 A | 9/1991 | Payton |

(56) References Cited

U.S. PATENT DOCUMENTS

| | | |
|---|---|---|
| 5,053,339 A | 10/1991 | Patel |
| 5,057,092 A | 10/1991 | Webster |
| 5,058,088 A | 10/1991 | Haas et al. |
| 5,071,347 A | 12/1991 | Mcguire |
| 5,078,707 A | 1/1992 | Peter |
| 5,084,037 A | 1/1992 | Barnett |
| 5,100,396 A | 3/1992 | Zamierowski |
| 5,112,324 A | 5/1992 | Wallace |
| 5,147,301 A | 9/1992 | Ruvio |
| 5,176,667 A | 1/1993 | Debring |
| 5,195,997 A | 3/1993 | Carns |
| 5,196,654 A | 3/1993 | Diflora et al. |
| 5,203,699 A | 4/1993 | Mcguire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,294,983 A | 3/1994 | Ersoz et al. |
| 5,295,983 A | 3/1994 | Kubo |
| 5,300,052 A | 4/1994 | Kubo |
| 5,304,749 A | 4/1994 | Crandell |
| 5,312,383 A | 5/1994 | Kubalak |
| 5,318,550 A | 6/1994 | Cermak et al. |
| 5,330,459 A | 7/1994 | Lavon et al. |
| 5,340,840 A | 8/1994 | Park et al. |
| 5,382,244 A | 1/1995 | Telang |
| 5,409,014 A | 4/1995 | Napoli et al. |
| 5,411,495 A | 5/1995 | Willingham |
| 5,423,784 A | 6/1995 | Metz |
| 5,456,246 A | 10/1995 | Schmieding et al. |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,582,604 A | 12/1996 | Ahr et al. |
| 5,592,950 A | 1/1997 | Kopelowicz |
| 5,605,161 A | 2/1997 | Cross |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,700,254 A | 12/1997 | Mcdowall et al. |
| 5,705,777 A | 1/1998 | Flanigan et al. |
| 5,752,944 A | 5/1998 | Dann et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,859,393 A | 1/1999 | Cummins et al. |
| 5,865,378 A | 2/1999 | Hollinshead et al. |
| 5,876,393 A | 3/1999 | Ahr et al. |
| 5,887,291 A | 3/1999 | Bellizzi |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,968,026 A | 10/1999 | Osborn et al. |
| 5,972,505 A | 10/1999 | Phillips et al. |
| 6,039,060 A | 3/2000 | Rower |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,220,050 B1 | 4/2001 | Cooksey |
| 6,244,311 B1 | 6/2001 | Hand et al. |
| 6,248,096 B1 | 6/2001 | Dwork et al. |
| 6,263,887 B1 | 7/2001 | Dunn |
| 6,283,246 B1 | 9/2001 | Nishikawa |
| 6,311,339 B1 | 11/2001 | Kraus |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,398,742 B1 | 6/2002 | Kim |
| 6,406,463 B1 | 6/2002 | Brown |
| 6,409,712 B1 | 6/2002 | Dutari et al. |
| 6,416,500 B1 | 7/2002 | Wada et al. |
| 6,423,045 B1 | 7/2002 | Wise et al. |
| 6,428,521 B1 | 8/2002 | Droll |
| 6,428,522 B1 | 8/2002 | Dipalma et al. |
| 6,446,454 B1 | 9/2002 | Lee et al. |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,524,292 B1 | 2/2003 | Dipalma et al. |
| 6,540,729 B1 | 4/2003 | Wada et al. |
| 6,547,771 B2 | 4/2003 | Robertson et al. |
| 6,569,133 B2 | 5/2003 | Cheng et al. |
| D476,518 S | 7/2003 | Doppelt |
| 6,592,560 B2 | 7/2003 | Snyder et al. |
| 6,610,038 B1 | 8/2003 | Dipalma et al. |
| 6,618,868 B2 | 9/2003 | Minnick |
| 6,620,142 B1 | 9/2003 | Flueckiger |
| 6,629,651 B1 | 10/2003 | Male et al. |
| 6,635,038 B2 | 10/2003 | Scovel |
| 6,652,495 B1 | 11/2003 | Walker |
| 6,666,850 B1 | 12/2003 | Ahr et al. |
| 6,685,684 B1 | 2/2004 | Falconer |
| 6,695,828 B1 | 2/2004 | Dipalma et al. |
| 6,700,034 B1 | 3/2004 | Lindsay et al. |
| 6,702,793 B1 | 3/2004 | Sweetser et al. |
| 6,706,027 B2 | 3/2004 | Harvie et al. |
| 6,732,384 B2 | 5/2004 | Scott |
| 6,736,977 B1 | 5/2004 | Hall et al. |
| 6,740,066 B2 | 5/2004 | Wolff et al. |
| 6,764,477 B1 | 7/2004 | Chen et al. |
| 6,783,519 B2 | 8/2004 | Samuelsson |
| 6,796,974 B2 | 9/2004 | Palumbo et al. |
| 6,814,547 B2 | 11/2004 | Childers et al. |
| 6,849,065 B2 | 2/2005 | Schmidt et al. |
| 6,857,137 B2 | 2/2005 | Otto |
| 6,885,690 B2 | 4/2005 | Aggerstam et al. |
| 6,888,044 B2 | 5/2005 | Fell et al. |
| 6,893,425 B2 | 5/2005 | Dunn et al. |
| 6,912,737 B2 | 7/2005 | Ernest et al. |
| 6,918,899 B2 | 7/2005 | Harvie |
| 6,979,324 B2 | 12/2005 | Bybordi et al. |
| 7,018,366 B2 | 3/2006 | Easter |
| 7,066,411 B2 | 6/2006 | Male et al. |
| 7,122,023 B1 | 10/2006 | Hinoki |
| 7,125,399 B2 | 10/2006 | Miskie |
| 7,131,964 B2 | 11/2006 | Harvie |
| 7,135,012 B2 | 11/2006 | Harvie |
| 7,141,043 B2 | 11/2006 | Harvie |
| D533,972 S | 12/2006 | La |
| 7,160,273 B2 | 1/2007 | Greter et al. |
| 7,171,699 B2 | 2/2007 | Ernest et al. |
| 7,171,871 B2 | 2/2007 | Kozak |
| 7,179,951 B2 | 2/2007 | Krishnaswamy-mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,219,764 B1 | 5/2007 | Forbes |
| 7,220,250 B2 | 5/2007 | Suzuki et al. |

(56) References Cited

U.S. PATENT DOCUMENTS

| | | |
|---|---|---|
| D562,975 S | 2/2008 | Otto |
| 7,335,189 B2 | 2/2008 | Harvie |
| 7,358,282 B2 | 4/2008 | Krueger et al. |
| 7,390,320 B2 | 6/2008 | Machida et al. |
| 7,438,706 B2 | 10/2008 | Koizumi et al. |
| 7,488,310 B2 | 2/2009 | Yang |
| 7,491,194 B1 | 2/2009 | Oliwa |
| D591,106 S | 4/2009 | Dominique et al. |
| 7,513,381 B2 | 4/2009 | Heng et al. |
| 7,520,872 B2 | 4/2009 | Biggie et al. |
| D593,801 S | 6/2009 | Wilson et al. |
| 7,540,364 B2 | 6/2009 | Sanderson |
| 7,549,512 B2 | 6/2009 | Newberry |
| 7,585,293 B2 | 9/2009 | Vermaak |
| 7,588,560 B1 | 9/2009 | Dunlop |
| 7,637,905 B2 * | 12/2009 | Saadat ................. A61B 1/0055 606/1 |
| 7,665,359 B2 | 2/2010 | Barber |
| 7,682,347 B2 | 3/2010 | Parks et al. |
| 7,687,004 B2 | 3/2010 | Allen |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns et al. |
| D625,407 S | 10/2010 | Koizumi et al. |
| 7,806,879 B2 | 10/2010 | Brooks et al. |
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,016,071 B1 | 9/2011 | Martinus et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,434,586 B2 | 5/2013 | Pawelski et al. |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,586,583 B2 | 11/2013 | Hamblin et al. |
| 8,652,112 B2 | 2/2014 | Johannison et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,145,879 B2 | 9/2015 | Pirovano et al. |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,381,108 B2 | 7/2016 | Longoni et al. |
| 9,382,047 B2 | 7/2016 | Schmidtner et al. |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,709,048 B2 | 7/2017 | Kinjo |
| 9,713,547 B2 | 7/2017 | Lee et al. |
| 9,732,754 B2 | 8/2017 | Huang et al. |
| 9,752,564 B2 | 9/2017 | Arceno et al. |
| 9,788,992 B2 | 10/2017 | Harvie |
| D804,907 S | 12/2017 | Sandoval |
| 9,868,564 B2 | 1/2018 | Mcgirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |

(56) References Cited

U.S. PATENT DOCUMENTS

| | | |
|---|---|---|
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| RE47,930 E | 4/2020 | Cho |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| D901,214 S | 11/2020 | Hu |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,378 B2 | 4/2021 | Ryu et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,168,420 B2 | 11/2021 | Kinugasa et al. |
| 11,179,506 B2 | 11/2021 | Barr et al. |
| 11,226,376 B2 | 1/2022 | Yamauchi et al. |
| 11,326,586 B2 | 5/2022 | Milner et al. |
| 11,369,508 B2 | 6/2022 | Ecklund et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |
| 11,389,318 B2 | 7/2022 | Radl et al. |
| 11,395,871 B2 | 7/2022 | Radl et al. |
| 11,426,303 B2 | 8/2022 | Davis et al. |
| 11,504,265 B2 | 11/2022 | Godinez et al. |
| 11,529,252 B2 | 12/2022 | Glithero et al. |
| 11,547,788 B2 | 1/2023 | Radl et al. |
| 11,806,266 B2 | 11/2023 | Sanchez et al. |
| D1,010,109 S | 1/2024 | Ecklund et al. |
| 11,857,716 B2 | 1/2024 | Lee et al. |
| 11,890,221 B2 | 2/2024 | Ulreich et al. |
| 11,925,575 B2 | 3/2024 | Newton |
| 2001/0037097 A1 | 11/2001 | Cheng et al. |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2003/0004436 A1 | 1/2003 | Schmidt et al. |
| 2003/0032931 A1 | 2/2003 | Grundke et al. |
| 2003/0032944 A1 | 2/2003 | Cawood |
| 2003/0073964 A1 | 4/2003 | Palumbo et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0015141 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147863 A1 | 7/2004 | Diaz et al. |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0176746 A1 | 9/2004 | Forral |
| 2004/0191919 A1 | 9/2004 | Unger et al. |
| 2004/0207530 A1 | 10/2004 | Nielsen |
| 2004/0236292 A1 | 11/2004 | Tazoe et al. |
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0155214 A1 | 7/2006 | Wightman |
| 2006/0171997 A1 | 8/2006 | Gruenbacher et al. |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0214553 A1* | 9/2007 | Carromba ............... A47K 11/12 4/144.4 |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |

(56) References Cited

U.S. PATENT DOCUMENTS

| | | |
|---|---|---|
| 2008/0215031 A1* | 9/2008 | Belfort ............ A61B 17/12099 606/192 |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0160882 A1 | 6/2010 | Lowe |
| 2010/0174250 A1 | 7/2010 | Hu et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0138064 A1 | 5/2013 | Stroebech et al. |
| 2013/0150813 A1 | 6/2013 | Gordon et al. |
| 2013/0245496 A1 | 9/2013 | Wells et al. |
| 2013/0245586 A1 | 9/2013 | Jha |
| 2013/0292537 A1 | 11/2013 | Dirico |
| 2014/0005647 A1* | 1/2014 | Shuffler ............ A61M 25/0147 29/592.1 |
| 2014/0031774 A1 | 1/2014 | Bengtson |
| 2014/0039432 A1 | 2/2014 | Dunbar et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0100276 A1 | 4/2017 | Joh |
| 2017/0128638 A1 | 5/2017 | Giezendanner et al. |
| 2017/0143534 A1 | 5/2017 | Sanchez |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1* | 9/2017 | Sanchez ................ A61F 5/4404 |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0042748 A1 | 12/2017 | Griffin |
| 2017/0348139 A1 | 12/2017 | Newton et al. |
| 2017/0354532 A1 | 12/2017 | Holt |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |

(56) References Cited

U.S. PATENT DOCUMENTS

| | | |
|---|---|---|
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1* | 8/2018 | Davis .................. A61F 5/451 |
| 2018/0256384 A1 | 9/2018 | Kasirye |
| 2018/0271694 A1 | 9/2018 | Fernandez et al. |
| 2018/0317892 A1 | 11/2018 | Catlin |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0247222 A1 | 8/2019 | Ecklund et al. |
| 2019/0247223 A1 | 8/2019 | Brun et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0008985 A1 | 1/2020 | Nguyen et al. |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1* | 3/2020 | von Weymarn-Schärli .................. A61M 25/0662 |
| 2020/0129322 A1 | 4/2020 | Leuckel |
| 2020/0171217 A9 | 6/2020 | Braga et al. |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0267787 A1 | 9/2021 | Nazemi |
| 2021/0275343 A1 | 9/2021 | Sanchez et al. |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0287689 A1 | 9/2022 | Johannes |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0395390 A1 | 12/2022 | Brooks |
| 2022/0395391 A1 | 12/2022 | Saunders et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0052238 A1 | 2/2023 | Oluwasogo |
| 2023/0062944 A1 | 3/2023 | Vollenberg et al. |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0099821 A1 | 3/2023 | Radl et al. |
| 2023/0105001 A1 | 4/2023 | Whittome et al. |
| 2023/0138269 A1 | 5/2023 | Abdelal et al. |
| 2023/0145365 A1 | 5/2023 | Martin et al. |
| 2023/0210504 A1 | 7/2023 | Kuroda et al. |
| 2023/0218426 A1 | 7/2023 | Hughett |
| 2023/0248562 A1 | 8/2023 | Sanchez et al. |

(56) References Cited

U.S. PATENT DOCUMENTS

| | | |
|---|---|---|
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277362 A1 | 9/2023 | Davis et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0009023 A1 | 1/2024 | Johannes et al. |
| 2024/0041638 A1 | 2/2024 | Johannes et al. |
| 2024/0058161 A1 | 2/2024 | Ulreich et al. |

FOREIGN PATENT DOCUMENTS

| | | |
|---|---|---|
| CA | 2165286 C | 9/1999 |
| CA | 2354132 A1 | 6/2000 |
| CA | 2488867 C | 8/2007 |
| CA | 3050918 A1 | 8/2018 |
| CA | 3098571 A1 | 11/2019 |
| CN | 2269203 Y | 12/1997 |
| CN | 1332620 A | 1/2002 |
| CN | 1533755 A | 10/2004 |
| CN | 1602825 A | 4/2005 |
| CN | 1720888 A | 1/2006 |
| CN | 2936204 Y | 8/2007 |
| CN | 101262836 A | 9/2008 |
| CN | 101522148 A | 9/2009 |
| CN | 102159159 A | 8/2011 |
| CN | 202184840 U | 4/2012 |
| CN | 102481441 A | 5/2012 |
| CN | 202463712 U | 10/2012 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A | 5/2016 |
| CN | 205849719 U | 1/2017 |
| CN | 106726089 A | 5/2017 |
| CN | 107847384 A | 3/2018 |
| CN | 107920912 A | 4/2018 |
| CN | 209285902 U | 8/2019 |
| CN | 110381883 A | 10/2019 |
| CN | 211198839 U | 8/2020 |
| CN | 112566550 A | 3/2021 |
| CN | 112603184 A | 4/2021 |
| CN | 114007493 A | 2/2022 |
| CN | 114375187 A | 4/2022 |
| CN | 116096332 A | 5/2023 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 4416094 A1 | 11/1995 |
| DE | 4236097 C2 | 10/1996 |
| DE | 19619597 A1 | 11/1997 |
| DE | 102005037762 B3 | 9/2006 |
| DE | 102011103783 A1 | 12/2012 |
| DE | 202015104597 U1 | 7/2016 |
| DK | 9600118 | 11/1996 |
| EP | 0032138 A2 | 7/1981 |
| EP | 0066070 B1 | 12/1982 |
| EP | 0140470 A1 | 5/1985 |
| EP | 0140471 B1 | 5/1988 |
| EP | 0274753 A2 | 7/1988 |
| EP | 0119143 B1 | 11/1988 |
| EP | 0483592 A1 | 5/1992 |
| EP | 0610638 A1 | 8/1994 |
| EP | 0613355 A1 | 9/1994 |
| EP | 0613355 B1 | 1/1997 |
| EP | 0787472 A1 | 8/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3753492 A1 | 12/2020 |
| EP | 3788992 A1 | 3/2021 |
| EP | 3576689 B1 | 3/2022 |
| EP | 3752110 B1 | 3/2022 |
| EP | 3787570 B1 | 3/2022 |
| EP | 4025163 A1 | 7/2022 |
| EP | 3463180 B1 | 3/2023 |
| GB | 1011517 A | 12/1965 |
| GB | 1467144 A | 3/1977 |
| GB | 2106784 A | 4/1983 |
| GB | 2148126 A | 5/1985 |
| GB | 2171315 A | 8/1986 |
| GB | 2181953 A | 5/1987 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2490327 A | 10/2012 |
| GB | 2507318 A | 4/2014 |
| GB | 2612752 A | 5/2023 |
| GE | 2106395 A | 4/1983 |
| IT | 201800009129 A1 | 4/2020 |
| JP | S5410596 A | 1/1979 |
| JP | S5410596 Y2 | 5/1979 |
| JP | S55155618 A | 12/1980 |
| JP | S5888596 U | 6/1983 |
| JP | S63107780 U | 7/1988 |
| JP | H0267530 A | 3/1990 |
| JP | H02103871 A | 4/1990 |
| JP | H02131422 A | 5/1990 |
| JP | H02131422 U | 11/1990 |
| JP | H0460220 A | 2/1992 |
| JP | H05123349 A | 5/1993 |
| JP | H05123350 A | 5/1993 |
| JP | 3087938 B2 | 10/1995 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |
| JP | 2003505152 A | 2/2003 |
| JP | 2003180722 A | 7/2003 |
| JP | 2004130056 A | 4/2004 |
| JP | 2004267530 A | 9/2004 |
| JP | 2005066011 A | 3/2005 |
| JP | 2005066325 A | 3/2005 |
| JP | 2005518237 A | 6/2005 |
| JP | 3749097 B2 | 12/2005 |
| JP | 2006026108 A | 2/2006 |
| JP | 3123547 B2 | 6/2006 |

(56) References Cited

FOREIGN PATENT DOCUMENTS

| | | |
|---|---|---|
| JP | 2006136492 A | 6/2006 |
| JP | 2006204868 A | 8/2006 |
| JP | 2007044494 A | 2/2007 |
| JP | 3132659 B2 | 5/2007 |
| JP | 4039641 B2 | 11/2007 |
| JP | 2009509570 A | 3/2009 |
| JP | 2010081981 A | 4/2010 |
| JP | 4640772 B2 | 12/2010 |
| JP | 2010536439 A | 12/2010 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2019525811 A | 9/2019 |
| JP | 2021120686 A | 8/2021 |
| JP | 2021522009 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2005051252 A1 | 6/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001532 A2 | 1/2017 |
| WO | 2017075226 A1 | 5/2017 |
| WO | 2017152198 A1 | 9/2017 |
| WO | 2017153357 A1 | 9/2017 |
| WO | 2017162559 A1 | 9/2017 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |

(56) References Cited

FOREIGN PATENT DOCUMENTS

| | | |
|---|---|---|
| WO | 2018235026 A1 | 12/2018 |
| WO | 2018235065 A1 | 12/2018 |
| WO | 2019004404 A1 | 1/2019 |
| WO | 2019041005 A1 | 3/2019 |
| WO | 2019044217 A1 | 3/2019 |
| WO | 2019044218 A1 | 3/2019 |
| WO | 2019044219 A1 | 3/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2019226826 A1 | 11/2019 |
| WO | 2019239433 A1 | 12/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020205939 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021046501 A1 | 3/2021 |
| WO | 2021086868 A1 | 5/2021 |
| WO | 2021094352 A1 | 5/2021 |
| WO | 2021094639 A1 | 5/2021 |
| WO | 2021102296 A1 | 5/2021 |
| WO | 2021107025 A1 | 6/2021 |
| WO | 2021138411 A1 | 7/2021 |
| WO | 2021138414 A1 | 7/2021 |
| WO | 2021154686 A1 | 8/2021 |
| WO | 2021155206 A1 | 8/2021 |
| WO | 2021173436 A1 | 9/2021 |
| WO | 2021188817 A1 | 9/2021 |
| WO | 2021195384 A1 | 9/2021 |
| WO | 2021205995 A1 | 10/2021 |
| WO | 2021207621 A1 | 10/2021 |
| WO | 2021211568 A1 | 10/2021 |
| WO | 2021211801 A1 | 10/2021 |
| WO | 2021216419 A1 | 10/2021 |
| WO | 2021216422 A1 | 10/2021 |
| WO | 2021231532 A1 | 11/2021 |
| WO | 2021247523 A1 | 12/2021 |
| WO | 2021257202 A1 | 12/2021 |
| WO | 2022006256 A1 | 1/2022 |
| WO | 2022031943 A1 | 2/2022 |
| WO | 2022035745 A1 | 2/2022 |
| WO | 2022051360 A1 | 3/2022 |
| WO | 2022054613 A1 | 3/2022 |
| WO | 2022066704 A1 | 3/2022 |
| WO | 2022076427 A2 | 4/2022 |
| WO | 2022086898 A1 | 4/2022 |
| WO | 2022098536 A1 | 5/2022 |
| WO | 2022115692 A1 | 6/2022 |
| WO | 2022125685 A1 | 6/2022 |
| WO | 2022140545 A1 | 6/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |
| WO | 2022187152 A1 | 9/2022 |
| WO | 2022192188 A1 | 9/2022 |
| WO | 2022192347 A1 | 9/2022 |
| WO | 2022216507 A1 | 10/2022 |
| WO | 2022222030 A1 | 10/2022 |
| WO | 2023014639 A1 | 2/2023 |
| WO | 2023014641 A1 | 2/2023 |
| WO | 2023018475 A2 | 2/2023 |
| WO | 2023034453 A1 | 3/2023 |
| WO | 2023038945 A1 | 3/2023 |
| WO | 2023038950 A1 | 3/2023 |
| WO | 2023049109 A1 | 3/2023 |
| WO | 2023049175 A1 | 3/2023 |
| WO | 2023086394 A1 | 5/2023 |
| WO | 2023149884 A1 | 8/2023 |
| WO | 2023149902 A1 | 8/2023 |
| WO | 2023149903 A1 | 8/2023 |
| WO | 2023154390 A1 | 8/2023 |
| WO | 2023191764 A1 | 10/2023 |
| WO | 2023244238 A1 | 12/2023 |

OTHER PUBLICATIONS

Merriam-Webster Dictionary, "Embed Definition & Meaning", https://www.merriam-webster.com/dictionary/embed (Year: 2023).*
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/899,956 mailed Apr. 19, 2021.

(56) References Cited

OTHER PUBLICATIONS

Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/905,400 mailed Dec. 2, 2020.
Non-Final Office Action for U.S. Appl. No. 16/905,400 mailed Jul. 22, 2021.

(56) References Cited

OTHER PUBLICATIONS

Non-Final Office Action for U.S. Appl. No. 17/088,272 mailed Jan. 25, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 17/088,272 mailed Aug. 5, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/478,180 mailed May 25, 2021.
U.S. Appl. No. 14/433,773, filed Apr. 3, 2020.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180 filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116 filed Feb. 18, 2021.
U.S. Appl. No. 17/330,657, filed May 26, 2021.
U.S. Appl. No. 17/378,015, filed Jul. 16, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/461,036 mailed Aug. 30, 2021.
U.S. Appl. No. 29/741,751, filed Jul. 15, 2020.
U.S. Appl. No. 62/452,437, filed Jan. 31, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172 filed Aug. 6, 2019.
U.S. Appl. No. 62/889,149, filed Aug. 20, 2019.
U.S. Appl. No. 62/938,447, filed Nov. 21, 2019.
U.S. Appl. No. 62/949,187 filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126 filed Aug. 11, 2020.
U.S. Appl. No. 63/067,542, filed Aug. 19, 2020.
U.S. Appl. No. 63/071,438, filed Aug. 28, 2020.
U.S. Appl. No. 63/073,545, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.

(56) References Cited

OTHER PUBLICATIONS

U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/214,551, filed Jun. 24, 2021.
U.S. Appl. No. 63/214,570, filed Jun. 24, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
Defendant and Counterclaim Plaintiff Sage Products, LLC's Answer, Defenses, and Counterclaims To Plaintiff's Amended Complaint, Nov. 1, 2019.
Memorandum Order, Feb. 2021, 14 pgs.
Sage's Initial Invalidity Contentions Regarding US Pat. Nos. 8,287,508; 10,226,375; and 10,390,989, May 29, 2020, 193 pages.
Exhibit A to PureWick's Fourth Supplemental Response to Interrogatory No. 3, Mar. 2021, 21 pages.
PureWick's Supplemental Response to Interrogatory No. 6 Exhibit C: U.S. Pat. No. 6,287,508, Sep. 2020, 21 pages.
Exhibit B to PureWick's Supplemental Response to Interrogatory No. 6: U.S. Pat. No. 8,287,508, 25 pages.
Exhibit B to PureWick's Supplemental Response to Interrogatory No. 6: U.S. Pat. No. 10,390,989, 26 pages.
Sage's Supplemental and Initial Invalidity Contentions Regarding U.S. Pat. No. 8,287,508; U.S. Pat. No. 10,226,375; U.S. Pat. No. 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. No. 8,287,508, U.S. Pat. No. 10,226,375, U.S. Pat. No. 10,390,989, and U.S. Pat. No. 10,376,407, 292 pages.
Boehringer CareDry System—Second Generation for Non-Invasive Urinary Management for Females, Mar. 2021, 3 pgs.
Exhibit B to PureWick's Supplemental Response to Interrogatory No. 6: U.S. Pat. No. 10,226,376, 38 pages.
Excerpts from the 508 (U.S. Pat. No. 8,278,508) Patent's Prosecution History, 2020, 99 pages.
Sage's Second Notice of Deposition of PureWick Corporation, C.A. No. 19-1508-MN, Feb. 2021, 10 pages.
Sage's First Notice of Deposition of PureWick Corporation, C.A. No. 19-1508-MN, Feb. 2021, 14 pages.
Sage's Supplemental Statement Regarding References and Combinations, C.A. No. 19-1508-MN, 3 pages.
Sixth Supplemental Responses to Sage Products' First Set of Interrogatories (No. 1-11) to PureWick Corporation, C.A. No. 19-1508-MN, Apr. 2021, 39 pages.
Seventh Supplemental Responses to Sage Products' First Set of Interrogatories (No. 1-11) to PureWick Corporation, C.A. No. 19-1508-MN, Apr. 2021, 41 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
PureWick's Response to Interrogatory No. 9 in *PureWick, LLC* v. *Sage Products, LLC*, Case No. 19-1508-MN, Mar. 23, 2020, 6 pages.
Sage's Preliminary Identification of Claim Elements and Proposed Constructions for U.S. Pat. No. 8,287,508, U.S. Pat. No. 10,226,376, U.S. Pat. No. 10,390,989 and U.S. Pat. No. 10,376,407, Case No. 19-1508-MN, 7 pages.
Decision Granting Institution of Inter Partes Review for U.S. Pat. No. 8,287,508, Case No. 2020-01426, Feb. 17, 2021, 39 pages.
Corrected Certificate of Service, Case No. IPR2020-01426, U.S. Pat. No. 8,287,508, 2020, 2 pages.
Declaration of Diane K. Newman Curriculum Vitae, Petition for Interparties Review, 2020, pp. 1-199.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, Omni Medical, 8 pages.
"AMXDmax In-Flight Bladder Relief", Omni Medical; Omni Medical Systems, Inc., 2015.
"AMXDX—Advanced Mission Extender Device Brochure", Omni Medical, Omni Brochure—http://www.omnimedicalsys.com/uploads/AMXDFixedWing.pdf, 2 pages.
"External Urine Management for Female Anatomy", https://www.stryker.com/US/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, Omni Presentation https://www.omnimedicalsys.com/uploads/AMXDmax_HSD.pdf, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Step by Step How Ur24 WorksHome", http://medicalpatentur24.com, last accessed Dec. 6, 2017, Aug. 30, 2017, 4 pages.
"Underwear that absorbs your period", Thinx!, https://www.shethinx.com/pages/thinx-it-works last accessed Jun. 24, 2020, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
Hollister, "Retracted Penis Pouch by Hollister", Vitality Medical.com, https://www.vitalitymedical.com/hollister-retracted-penis-pouch.html last accessed Jun. 24, 2020, 6 pages.
Jennewein, "Connect Graduates 7 Startups in Tech, Life Sciences", https://timesofsandiego.com/business/2015/08/16/connect-graduates-7-startups-in-tech-life-sciences/, Aug. 2015, 2 pages.
MacAulay, et al., "A Noninvasive Continence Management System: Development and Evaluation of a Novel Toileting Device for Women", The Wound, Ostomy and Continence Nurses Society, vol. 34 No. 6, 2007, pp. 641-648.

(56) References Cited

OTHER PUBLICATIONS

Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Purewick, "Incontinence Relief for Women", Presentation, Sep. 23, 2015, 7 pages.
Pytlik, "Super Absorbent Polymers", University of Buffalo, http://www.courses.sens.buffalo.edu/ce435/Diapers/Diapers.html, accessed on Feb. 17, 2017.
Sachtman, "New Relief for Pilots? It Depends", Wired, https://www.wired.com/2008/05/pilot-relief/, 2008, 2 pages.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Feb. 15, 2023.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 17/662,700 mailed Jan. 30, 2023.
Corrected Notice of Allowability for U.S. Appl. No. 17/330,657 mailed Dec. 9, 2021.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/904,868 mailed Mar. 10, 2022.
Final Office Action for U.S. Appl. No. 16/905,400 mailed Dec. 9, 2021.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/451,345 mailed May 3, 2023.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2020/057562 mailed Jan. 27, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
Non-Final Office Action for U.S. Appl. No. 17/051,585 mailed Mar. 29, 2023.
Non-Final Office Action for U.S. Appl. No. 17/179,116 mailed Mar. 24, 2023.
Non-Final Office Action for U.S. Appl. No. 17/330,657 mailed Aug. 11, 2021.
Non-Final Office Action for U.S. Appl. No. 17/444,792 mailed Feb. 10, 2023.
Non-Final Office Action for U.S. Appl. No. 17/446,256 mailed Apr. 13, 2023.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.

(56) References Cited

OTHER PUBLICATIONS

International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/044107 mailed Dec. 23, 2022.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 11, 2023.
Non-Final Office Action for U.S. Appl. No. 16/433,773 mailed Apr. 21, 2022.
Non-Final Office Action for U.S. Appl. No. 16/449,039 mailed Apr. 27, 2023.
Non-Final Office Action for U.S. Appl. No. 16/449,039 mailed Dec. 8, 2021.
Non-Final Office Action for U.S. Appl. No. 16/452,145 mailed Mar. 28, 2023.
Non-Final Office Action for U.S. Appl. No. 16/452,145 mailed Sep. 28, 2021.
Non-Final Office Action for U.S. Appl. No. 16/452,258 mailed Apr. 26, 2023.
Non-Final Office Action for U.S. Appl. No. 16/452,258 mailed Sep. 28, 2021.
Non-Final Office Action for U.S. Appl. No. 16/478,180 mailed Dec. 20, 2022.
Non-Final Office Action for U.S. Appl. No. 16/478,180 mailed Oct. 22, 2021.
Non-Final Office Action for U.S. Appl. No. 16/904,868 mailed Mar. 15, 2023.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 17/051,550 mailed Dec. 15, 2022.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/501,591 mailed Apr. 25, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/662,700 mailed Jul. 22, 2022.
Non-Final Office Action for U.S. Appl. No. 29/741,751 mailed Jan. 18, 2022.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/461,036 mailed Feb. 22, 2023.
Notice of Allowance for U.S. Appl. No. 17/461,036 mailed Oct. 6, 2022.
Notice of Allowance for U.S. Appl. No. 17/662,700 mailed Mar. 28, 2023.
Notice of Allowance for U.S. Appl. No. 17/663,046 mailed Jan. 30, 2023.
Notice of Allowance for U.S. Appl. No. 29/741,751 mailed Jun. 9, 2022.
Restriction Requirement for U.S. Appl. No. 16/433,773 mailed Dec. 7, 2021.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/646,771 mailed Apr. 6, 2023.

(56) References Cited

OTHER PUBLICATIONS

Text Messages to Lorena Eckert Re Prototype PureWick Holder dated Apr. 16, 2022.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/384,196 filed Dec. 19, 2016.
U.S. Appl. No. 16/245,726, filed Jan. 11, 2019.
U.S. Appl. No. 17/394,055, filed Aug. 4, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152 filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155 filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109 filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163 filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121 filed Mar. 21, 2023.
U.S. Appl. No. 18/247,986, filed Apr. 5, 2023.
U.S. Appl. No. 18/299,788, filed Apr. 13, 2023.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/967,158 filed Jan. 26, 2020.
U.S. Appl. No. 62/967,977, filed Jan. 30, 2020.
U.S. Appl. No. 62/991,754, filed Mar. 19, 2020.
U.S. Appl. No. 63/008,112 filed Apr. 10, 2020.
U.S. Appl. No. 63/073,553, filed Sep. 2, 2020.
U.S. Appl. No. 63/094,646, filed Oct. 21, 2020.
U.S. Appl. No. 63/109,084, filed Nov. 3, 2020.
U.S. Appl. No. 63/133,892, filed Jan. 5, 2021.
U.S. Appl. No. 63/138,878, filed Jan. 19, 2021.
U.S. Appl. No. 63/191,558, filed May 21, 2021.
U.S. Appl. No. 63/192,289, filed May 24, 2021.
U.S. Appl. No. 63/193,891, filed May 27, 2021.
U.S. Appl. No. 63/208,262, filed Jun. 8, 2021.
U.S. Appl. No. 63/215,017, filed Jun. 25, 2021.
U.S. Appl. No. 63/228,244, filed Aug. 2, 2021.
U.S. Appl. No. 63/230,897, filed Aug. 9, 2021.
U.S. Appl. No. 63/241,328, filed Sep. 7, 2021.
U.S. Appl. No. 63/247,491, filed Sep. 23, 2021.
U.S. Appl. No. 63/299,208, filed Jan. 13, 2022.
U.S. Appl. No. 63/308,190 filed Feb. 9, 2022.
*PureWick Corporation* v. *Sage Products*, LLC Transcripts vol. 5, Apr. 1, 2022, 72 pages.
*PureWick Corporation* v. *Sage Products*, LLC Transcripts vol. 1, Mar. 28, 2022, 99 pages.
*PureWick Corporation* v. *Sage Products*, LLC Transcripts vol. 2, Mar. 29, 2022, 106 pages.
*PureWick Corporation* v. *Sage Products*, LLC Transcripts vol. 3, Mar. 30, 2022, 115 pages.
*PureWick Corporation* v. *Sage Products*, LLC Transcripts vol. 4, Mar. 31, 2022, 117 pages.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
"Rising Warrior Insulated Gallon Jug Cover", https://www.amazon.com/Rising-Warrior-Insulated-Sleeve, 2021, 2 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hwang , et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.

(56) References Cited

OTHER PUBLICATIONS

Jeong, et al., "A nontransferring dry adhesive with hierarchical polymer nanohairs", PNAS, Apr. 7, 2009, pp. 5639-5644.
Jeong, et al., "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Parness, et al., "A microfabricated wedge-shaped adhesive array displaying gecko-like dynamic adhesion, directionality", J.R. Soc. Interface, 2009, pp. 1223-1232.
Pieper, et al., "An external urine-collection device for women: A clinical trial", Journal of ER Nursing, vol. 20, No. 2, Mar./Apr. 1993, pp. 51-55.
Tsipenyuk, et al., "Use of biomimetic hexagonal surface texture in friction against lubricated skin", Journal of The Royal Society—Interface, 2014, pp. 1-6.
Vinas, "A Solution For An Awkward—But Serious—Subject", http://www.aero-news.net/index.cfm?do=main.textpost&id=69ae2bb1-838b-4098-a7b5-7flbb2505688 last accessed Feb. 8, 2021, 3 pages.
U.S. Appl. No. 17/614,173 filed Nov. 24, 2021.
Advisory Action for U.S. Appl. No. 16/478,180 mailed Sep. 7, 2023.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/444,792 mailed Aug. 25, 2023.
Advisory Action for U.S. Appl. No. 17/451,345 mailed Oct. 20, 2023.
Final Office Action for U.S. Appl. No. 16/369,676 mailed Aug. 31, 2023.
Final Office Action for U.S. Appl. No. 16/433,773 mailed Oct. 10, 2023.
Final Office Action for U.S. Appl. No. 16/449,039 mailed Nov. 21, 2023.
Final Office Action for U.S. Appl. No. 16/478,180 mailed May 31, 2023.
Final Office Action for U.S. Appl. No. 16/904,868 mailed Nov. 2, 2023.
Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/448,811 mailed Aug. 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/653,137 mailed Sep. 21, 2023.
Final Office Action for U.S. Appl. No. 17/655,464 mailed Sep. 1, 2023.
International Search Report and Written Opinion from International Application No. PCT/US2022/043818 mailed Mar. 24, 2023.
International Search Report and Written Opinion from International Application No. PCT/US2022/044208 mailed May 8, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
Issue Notification for U.S. Appl. No. 16/245,726 mailed Oct. 18, 2023.
Issue Notification for U.S. Appl. No. 17/461,036 mailed Oct. 11, 2023.
Non-Final Office Action for U.S. Appl. No. 16/452,145 mailed Nov. 2, 2023.
Non-Final Office Action for U.S. Appl. No. 16/478,180 mailed Nov. 7, 2023.
Non-Final Office Action for U.S. Appl. No. 17/051,399 mailed Aug. 18, 2023.
Non-Final Office Action for U.S. Appl. No. 17/051,550 mailed Oct. 24, 2023.
Non-Final Office Action for U.S. Appl. No. 17/326,980 mailed Jul. 11, 2023.
Non-Final Office Action for U.S. Appl. No. 17/444,792 mailed Nov. 17, 2023.
Non-Final Office Action for U.S. Appl. No. 17/446,654 mailed Sep. 8, 2023.
Non-Final Office Action for U.S. Appl. No. 17/453,560 mailed Oct. 16, 2023.
Non-Final Office Action for U.S. Appl. No. 17/645,821 mailed Oct. 25, 2023.
Non-Final Office Action for U.S. Appl. No. 17/646,771 mailed Jul. 5, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/808,354 mailed Nov. 28, 2023.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/461,036 mailed Jun. 30, 2023.
Notice of Allowance for U.S. Appl. No. 17/662,700 mailed Jul. 28, 2023.
Notice of Allowance for U.S. Appl. No. 17/662,700 mailed Nov. 15, 2023.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/645,821 mailed Jul. 12, 2023.
Restriction Requirement for U.S. Appl. No. 17/657,474 mailed Jun. 30, 2023.
Restriction Requirement for U.S. Appl. No. 18/134,857 mailed Oct. 23, 2023.
U.S. Appl. No. 17/451,719, filed Oct. 19, 2021.
U.S. Appl. No. 17/664,487, filed May 23, 2022.
U.S. Appl. No. 18/259,626, filed Jun. 28, 2023.

(56) References Cited

OTHER PUBLICATIONS

U.S. Appl. No. 18/260,122 filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 63/150,640, filed Feb. 18, 2021.
U.S. Appl. No. 63/596,012, filed Nov. 3, 2023.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
Advisory Action for U.S. Appl. No. 16/433,773 mailed Dec. 29, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/904,868 mailed Jan. 2, 2024.
Advisory Action for U.S. Appl. No. 17/179,116 mailed Jan. 8, 2024.
Advisory Action for U.S. Appl. No. 17/446,256 mailed Dec. 8, 2023.
Advisory Action for U.S. Appl. No. 17/446,654 mailed Apr. 15, 2024.
Advisory Action for U.S. Appl. No. 17/450,864 mailed on Mar. 21, 2024.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/657,474 mailed Mar. 13, 2024.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 17/051,399 mailed Jan. 8, 2024.
Final Office Action for U.S. Appl. No. 17/444,792 mailed Apr. 3, 2024.
Final Office Action for U.S. Appl. No. 17/446,654 mailed Jan. 31, 2024.
Final Office Action for U.S. Appl. No. 17/450,864 mailed Dec. 28, 2023.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 17/808,354 mailed Apr. 10, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/904,868 mailed Mar. 12, 2024.
Non-Final Office Action for U.S. Appl. No. 17/051,585 mailed Jan. 8, 2024.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/446,256 mailed Feb. 13, 2024.
Non-Final Office Action for U.S. Appl. No. 17/447,123 mailed Jan. 24, 2024.
Non-Final Office Action for U.S. Appl. No. 17/451,345 mailed Jan. 17, 2024.
Non-Final Office Action for U.S. Appl. No. 17/451,354 mailed Apr. 4, 2024.
Non-Final Office Action for U.S. Appl. No. 17/597,673 mailed Mar. 20, 2024.
Non-Final Office Action for U.S. Appl. No. 17/653,137 mailed Jan. 18, 2024.

(56) References Cited

OTHER PUBLICATIONS

Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/664,914 mailed Jan. 31, 2024.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/164,800 mailed Mar. 22, 2024.
Non-Final Office Action for U.S. Appl. No. 18/198,464 mailed Dec. 7, 2023.
Notice of Allowance for U.S. Appl. No. 16/449,039 mailed Mar. 28, 2024.
Notice of Allowance for U.S. Appl. No. 17/051,550 mailed Feb. 7, 2024.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/657,474 mailed Mar. 5, 2024.
Notice of Allowance for U.S. Appl. No. 17/662,700 mailed Mar. 6, 2024.
Notice of Allowance for U.S. Appl. No. 18/198,464 mailed Apr. 17, 2024.
Restriction Requirement for U.S. Appl. No. 17/667,097 mailed Mar. 20, 2024.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/444,792, filed Aug. 10, 2021.
U.S. Appl. No. 18/249,577, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/415,080, filed Jan. 17, 2024.
U.S. Appl. No. 18/426,795, filed Jan. 30, 2024.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/681,987, filed Feb. 7, 2024.
U.S. Appl. No. 18/682,006, filed Feb. 7, 2024.
U.S. Appl. No. 18/687,117 filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 63/561,893, filed Dec. 11, 2023.
U.S. Appl. No. 63/608,553, filed Dec. 11, 2023.
Wikipedia Article, "Decibel", https://web.archive.org/web/20200415219177/https://en.wikipedia.org/wiki/Decibel last accessed Mar. 11, 2024, 21 pages.
Wikipedia Article, "Fiberglass", https://web.archive.org/web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder_(Geometrie)&oldid=154862081, version of Jun. 1, 2016, 7 pages.

\* cited by examiner

FLUID COLLECTION SYSTEMS INCLUDING AT LEAST ONE TENSIONING ELEMENT

CROSS-REFERENCE TO RELATED APPLICATION(S)

This application claims priority to U.S. Provisional Patent Application No. 63/008,511 filed on Oct. 7, 2020, the disclosure of which is incorporated herein, in its entirety, by this reference.

BACKGROUND

A person or animal may have limited or impaired mobility such that typical urination processes are challenging or impossible. For example, a person may experience or have a disability that impairs mobility. A person may have restricted travel conditions such as those experienced by pilots, drivers, and workers in hazardous areas. Additionally, sometimes urine collection is needed for monitoring purposes or clinical testing.

Urinary catheters, such as a Foley catheter, can be used to address some of these circumstances, such as incontinence. Unfortunately, urinary catheters can be uncomfortable, painful, and can lead to complications, such as infections. Additionally, bed pans, which are receptacles used for the toileting of bedridden patients are sometimes used. However, bedpans can be prone to discomfort, spills, and other hygiene issues.

SUMMARY

Embodiments disclosed herein are directed to fluid collection systems and methods of using the same. In an embodiment, a fluid collection system is disclosed. The fluid collection system includes a fluid collection assembly. The fluid collection assembly includes a fluid impermeable barrier defining a chamber, at least one opening, and at least one fluid outlet. The fluid collection assembly also includes t least one porous material disposed in the chamber. The fluid collection system also includes at least one tensioning element at least partially disposed in the fluid collection assembly. The at least one tensioning element is configured to switch from a relaxed state when the at least one tensioning element has substantially no tension force applied thereto and a tensioned state when the at least one tensioning element has a tension force applied thereto. Switching the at least one tensioning element between the relaxed state and the tensioned state changes a curvature of at least a portion of the fluid collection assembly.

In an embodiment, a method of using a fluid collection system. The method includes positioning at least one opening of a fluid collection assembly adjacent to a female urethral opening. The fluid collection assembly includes a fluid impermeable barrier defining a chamber, at least one opening, and at least one fluid outlet. The fluid collection assembly also includes at least one porous material disposed in the chamber. The fluid collection system further comprises at least one tensioning element at least partially disposed in the fluid collection assembly. The method also includes tensioning at least one tensioning element to switch the tensioning element from a relaxed state to a tensioned state to change a curvature of the fluid collection assembly.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1A:
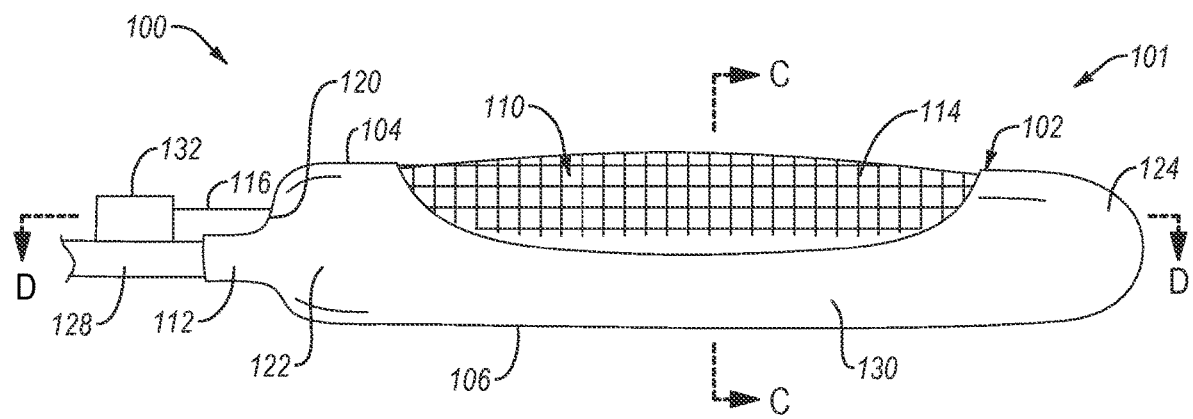
FIGS. 1A and 1B are isometric views of a fluid collection system that includes a fluid collection assembly in a first shape and a second shape, respectively, according to an embodiment.

Embodiments disclosed herein are directed to fluid collection systems and methods of using the same. An example fluid collection system includes a fluid collection assembly and at least one tensioning element (e.g., wire). The fluid collection assembly includes a fluid impermeable barrier that defines at least a chamber, at least one opening, and at least one fluid outlet. The fluid collection assembly also includes at least one porous material disposed in the chamber. The at least one tensioning element of the fluid collection system is configured to switch from a relaxed state and a tensioned state. The at least one tensioning element is in the relaxed state when substantially no external tensile force is applied thereto and the tensioned state when an external tensile force is applied thereto. The at least one tensioning element is configured to change a curvature of at least a portion of the fluid collection assembly, for example, by switching the tensioning element between the relaxed state and the tensioned state.

During use, the fluid collection assembly is positioned adjacent to a urethral opening (e.g., vagina) of the patient. One or more bodily fluids (e.g., urine, blood, etc.) that are discharged from the urethral opening of the patient flow through the opening and into the chamber. The bodily fluids that enter the chamber are received into the porous material and are directed towards the fluid outlet. The bodily fluids may be removed from the chamber through the fluid outlet, for example, when a suction force from a vacuum source is applied to the fluid outlet.

Generally, the fluid collection assembly conforms to the shape of the region about the urethral opening to prevent gaps between the fluid collection assembly and the region about the urethral opening. For example, bodily fluids may leak (e.g., do not enter the chamber and/or do not remain in the chamber) through gaps between the fluid collection assembly and the region about the patient. Such leaks may be embarrassing to the patient using the fluid collection assembly, cause the skin of the patient to remain moist which may cause skin degradation (e.g., rash) and general discomfort, and create unsanitary situations.

The region of the patient about the urethral opening may vary in size and shape depending on the patient. Some conventional fluid collection assemblies are manually bent to conform to the shape of the region about the urethral opening to prevent gaps between the conventional fluid collection assemblies and the region about the patient. Contact between the thighs of the patient and the conventional fluid collection assemblies maintains the bent form of the conventional fluid collection assemblies. However, relatively thin or skinny patients may have too small of thighs to maintain contact with the conventional fluid collection assemblies while forgetful patients (e.g., confused patients, young children, patients with dementia) may move their legs such that the thighs no longer contact the conventional fluid collection assemblies, either of which may cause the conventional fluid collection assembly to lose the bent shape thereof.

Embodiments of fluid collection systems disclosed herein (e.g., fluid collection assemblies including at least one tensioning element) amount to an improvement to systems that include such conventional fluid collection assemblies. As previously discussed, the fluid collection systems disclosed herein include at least one tensioning element. The at least one tensioning element is configured to control the curvature of at least a portion of the fluid collection assembly such that at least a portion of the fluid collection generally conforms to the shape (e.g., curvature) of the region about the urethral opening. The at least one tensioning element may also allow the fluid collection assembly to maintain the shape thereof without relying on contact between the fluid collection assembly and the thighs of the patient. As such, the at least one tensioning element may minimize gaps between the fluid impermeable barrier and the region about the urethral opening through which bodily fluids may flow.

Figure 1B:
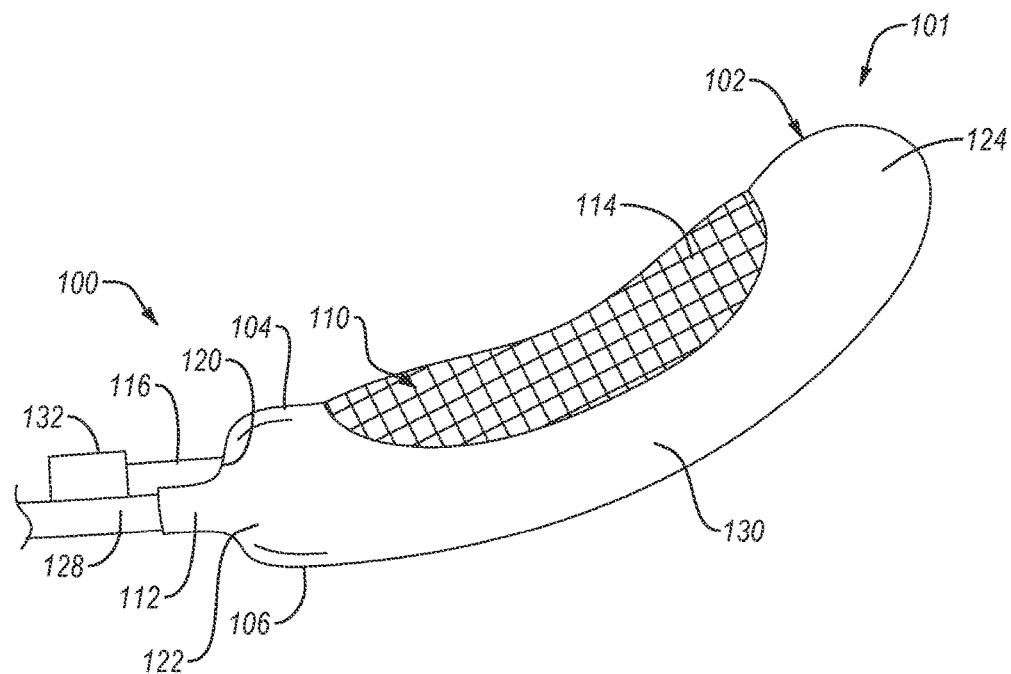
Figure 1C:
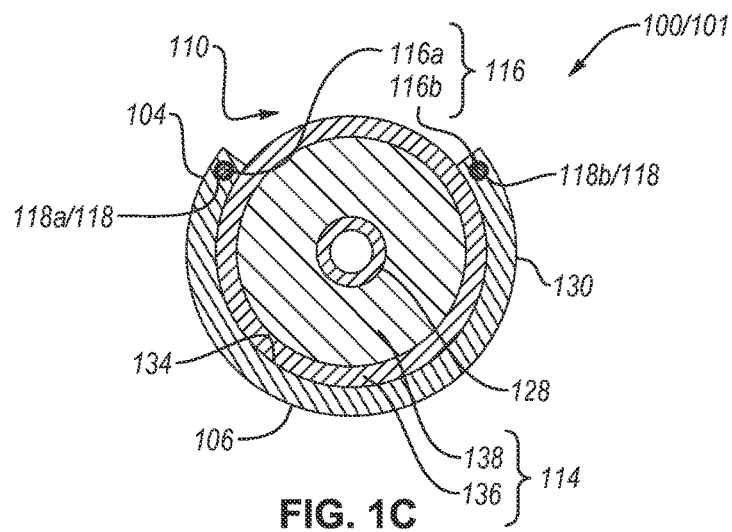
FIGS. 1C and 1D are cross-sectional schematics of the fluid collection assembly taken along planes C-C and D-D shown in FIG. 1A, respectively.
Figure 1D:
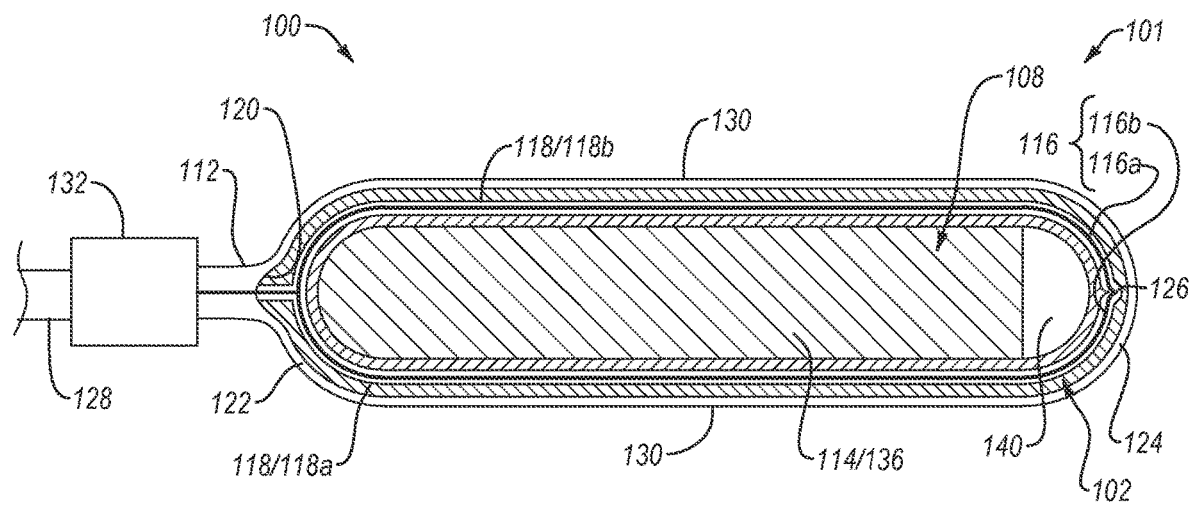

At least a portion of the at least one tensioning element may be disposed in the fluid collection assembly. The fluid collection assembly may exhibit a first (e.g., initial) shape when the tensioning element is in the relaxed state. The at least one tensioning element may have an external tensile force applied thereto to switch the tensioning element to the tensioned state thereof. The tensile force applied to the at least one tensioning element may cause the at least one tensioning element to apply a compressive force to the portions of the fluid collection assembly thereabout. The compressive force decreases a length of the portions of the fluid collection assembly adjacent to the at least one tensioning element while the portions of the fluid collection assembly that are spaced from the at least one tensioning element may exhibit no length change or a smaller length change than the portions of the fluid collection assembly adjacent to the at least one tensioning element. The decreased length of the portions of the fluid collection assembly adjacent to the at least one tensioning element may cause the fluid collection assembly to bend such that the fluid collection assembly exhibits a second shape that is different than the first shape. In an example, the first shape of the fluid collection assembly may exhibit a straight or substantially straight shape when the at least one tensioning element is in the relaxed state. In such an example, applying a tensile force to the at least one tensioning element may cause the fluid collection assembly to exhibit a bent shape. In an example, the fluid collection assembly may exhibit a curved shape when the at least one tensioning element is in the relaxed state. In such an example, applying a tensile force to the at least one tensioning element may increase the curvature of the fluid collection assembly or may straighten the fluid collection assembly FIGS. 1A and 1B are isometric view of a fluid collection system 100 that includes a fluid collection assembly 101 in a first shape and a second shape, respectively, according to an embodiment. FIGS. 1C and 1D are cross-sectional schematics of the fluid collection assembly 101 taken along planes C-C and D-D shown in FIG. 1A, respectively. The fluid collection assembly 101 include a fluid impermeable barrier 102. The fluid impermeable barrier 102 includes a proximal surface 104 that is configured to be positioned adjacent to an patient during use and a distal surface 106 opposite the proximal surface 104. The fluid impermeable barrier 102 defines at least a chamber 108, at least one opening 110 that is defined by the proximal surface 104, and at least one fluid outlet 112. The fluid collection assembly 101 also includes at least one porous material 114 disposed in the chamber 108. The fluid collection system 100 also includes at least one tensioning element 116. At least a portion of the tensioning element 116 is disposed in the fluid collection assembly 101.

Figure 2A:
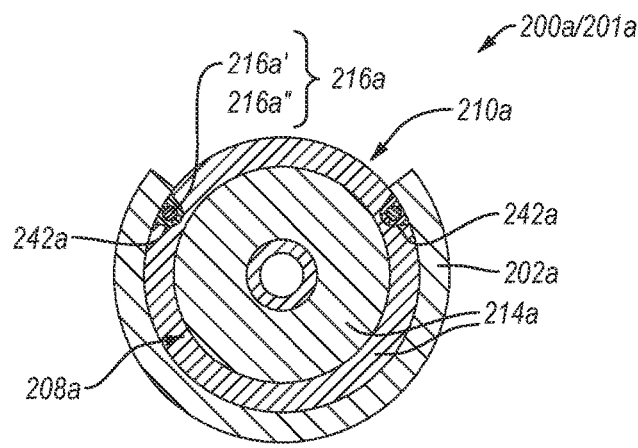
FIGS. 2A-2E are cross-sectional schematics of fluid collection systems having at least one tensioning element positioned at different locations of the fluid collection assembly, according to different embodiments.
Figure 2B:
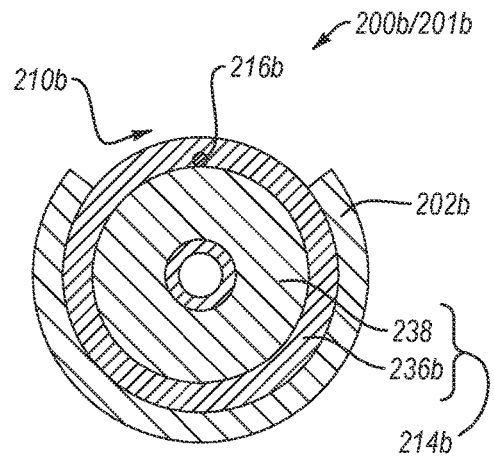
Figure 2C:
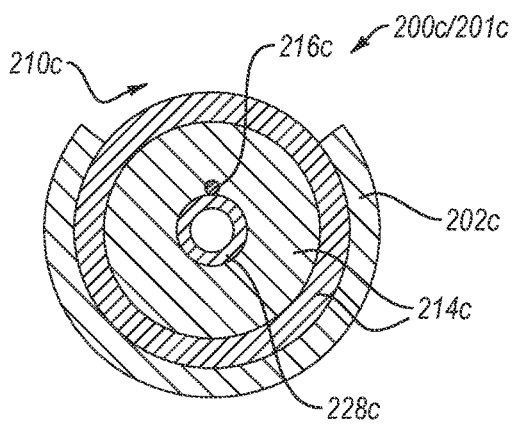

The tensioning element 116 is a longitudinally extending element that may be at least partially disposed in the fluid collection assembly 101. The tensioning element 116 may include, for example, at least one wire, at least one sheet, at least one thread, a monofilament, a plurality of monofilaments (e.g., a plurality of monofilaments twisted or braided together), a rope or thread, combinations of the foregoing, any other device that may have a tensile force applied thereto. Generally, the tensioning element 116 is flexible, which allows the tensioning element 116 to conform to the shape of the fluid collection assembly 101 when the tensioning element 116 is in the relaxed state and the exhibit a shape change when switching between the relaxed and tensioned states. For example, the tensioning element 116 may be formed from a fabric, a polymer (e.g., polyethylene, polypropylene, polyvinyl chloride, etc.), a thin metal wire, a composite, or combinations thereof. In some examples (as shown in FIGS. 2A-2C), the tensioning element 116 may be exposed to the bodily fluids that are present in the chamber 108. In such examples, the tensioning element 116 may be formed from a material that is resistant to the bodily fluids or coated with a material that is resistant to the bodily fluids. Examples of material that are resistant to the bodily fluids may include oxidation resistant materials or other chemically inert materials. For instance, when the tensioning element 116 is not formed from a material that is resistant to the bodily fluids, the bodily fluids may cause the tensioning element 116 to release contaminants (e.g., ions, microparticles) into the bodily fluids. Backflow of the bodily fluids may cause the contaminants to come in contact with and irritate the skin of the individual.

The tensioning element 116 includes an fixed portion 126 (shown in FIG. 1D) that is fixedly secured to one or more components of the fluid collection assembly 101, such as the fluid impermeable barrier 102, the porous material 114, or the conduit 128. In an example, as illustrated, the fixed portion 126 is at the terminal end of the tensioning element 116. In an example, the fixed portion 126 may be spaced from the terminal end of the tensioning element 116. In such an example, the fixed portion 126 is generally near (e.g., within about 1 mm, within about 2.5 mm, within about 5 mm, or within about 1 cm) of the terminal end of the tensioning element 116 since any portion of the tensioning element 116 between the terminal end and the fixed portion 126 may be extraneous (e.g., may be unable to switch between relaxed and tensioned states). The fixed portion 126 is configured to maintain a position thereof relative to the component to which it is attached when a tensile force is applied to the tensioning element 116. For example, the fixed portion 126 allows a tensile force to be applied to the tensioning element 116 when tensioning element 116 is pulled on since the fixed portion 126 acts as an anchor.

Figure 2D:
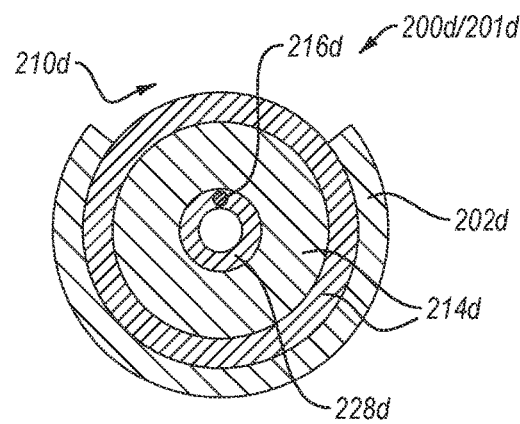
Figure 2E:
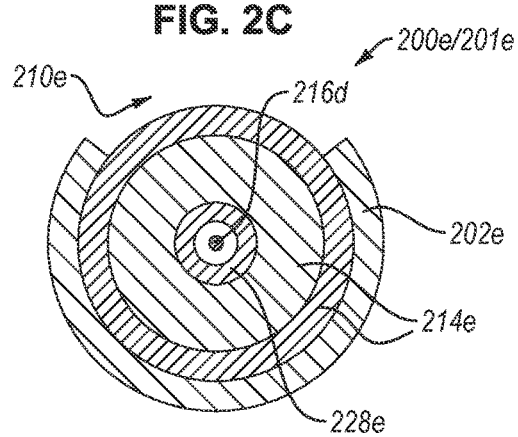

The component to which the fixed portion 126 is attached may be selected to be a component of the fluid collection assembly 101 to which the terminal end of the tensioning element 116 is adjacent. For example, in the illustrated embodiment, at least a portion of the tensioning element 116 is within the fluid impermeable barrier 102 and, unless the tensioning element 116 moves out of the fluid impermeable barrier 102, the fixed portion 126 is attached to the fluid impermeable barrier 102. Alternatively, the fixed portion 126 may be attached to the fluid impermeable barrier 102 and/or the porous material 114 when at least a portion of the tensioning element 116 is between the fluid impermeable barrier 102 and the porous material 114 (FIG. 2A), attached to the porous material 114 when at least a portion of the tensioning element 116 is disposed within the porous material 114 (FIG. 2B), attached to the porous material 114 and/or the conduit 128 when at least a portion of the tensioning element 116 is between the porous material 114 and the conduit 128 (FIG. 2C), or attached to the conduit 128 when at least a portion of the conduit is positioned within the conduit 128 (FIGS. 2D and 2E). The fixed portion 126 may be attached to the component of the fluid collection assembly 101 using any suitable attachment technique, such as via an adhesive, welding (e.g., ultrasonic welding), tape, crimping, or a knot.

As previously discussed, the tensioning element 116 is configured to switch between a relaxed state and a tensioned state. The tensioning element 116 switches from the relaxed state to the tensioned state by applying an external tensile force to the tensioning element 116. The tensile force may be applied to the tensioning element 116 by pulling on portions of the tensioning element 116 that are not disposed within the fluid collection assembly 101. The tensioning element 116 may switch from the tensioned state to a relaxed state by removing the tensile force form the tensioning element 116.

Switching the tensioning element 116 between the relaxed state and the tensioned state is configured to change the shape of the fluid collection assembly 101. For example, switching the tensioning element 116 from the relaxed state to the tensioned state causes the tensioning element 116 to apply a greater compressive force on a first portion of the fluid collection assembly 101 than a second portion of the fluid collection assembly. As used herein, the first portion of the fluid collection assembly 101 refers to a portion of the fluid collection assembly 101 adjacent to the tensioning element 116 and the second portion of the fluid collection assembly 101 refers to a portion of the fluid collection assembly 101 that is spaced from the tensioning element 116. For example, the tensile force may cause the fixed portion 126 of the tensioning element 116 to pull the component to which it is attached in a direction that is parallel to the tensile force. Pulling the component in such a manner applies a compressive force to first portion the fluid collection assembly 101. The compressive force causes a length of the first portion of the fluid collection assembly to decrease while a length of the second portion of the fluid collection assembly remains the same or decrease at a rate that is less than the first portion. The different changes of length between the first and second portions of the fluid collection assembly 101 causes the shape of the fluid collection assembly 101 to change. For example, the decreased length change of the first portion relative to the second portion causes the fluid collection assembly 101 to bend towards the first portion. Switching the tensioning element 116 from the tensioned state to the relaxed state causes the lengths of the first and second portions to generally return to their original lengths. In other words, the length of the first portion increases more than the second portion when the tensioning element 116 switches from the tensioned state to the relaxed state thereby returning the fluid collection assembly to its original shape.

The amount of the tensioning element 116 changes the shape of the fluid collection assembly 101 may be controlled based on the magnitude of the tensile force applied to the tensioning element 116. For example, increasing the tensile force to the tensioning element 116 may cause the fluid collection assembly 101 to deviate more from the first (e.g., initial) shape that the fluid collection assembly 101 exhibits when the tensioning element 116 is in the relaxed state. Further, decreasing the tensile force to the tensioning element 116 may cause the fluid collection assembly 101 to deviate less from the first shape.

The position of the tensioning element 116 in the fluid collection assembly 101 may at least partially dictate how the tensioning element 116 changes the shape of the fluid collection assembly 101 when the tensioning element 116 switches between the relaxed and tensioned states thereof. In other words, the position of the tensioning element 116 in the fluid collection assembly 101 at least partially dictates which portions of the fluid collection assembly 101 are the first portion and the second portion. Generally, the tensioning element 116 is substantially centered between the lateral surfaces 130 of the fluid impermeable barrier 102 that extend between the proximal and distal surfaces 104, 106 of the fluid impermeable barrier 102. This ensures that the opening 110 may extend along the vagina instead of bending to the side when the tensioning element 116 in the tensioned state. However, the tensioning element 116 may be positioned closer to the proximal surface 104 or the distal surface 106. In an embodiment, as illustrated, the tensioning element 116 is positioned closer to the proximal surface 104 than the distal surface 106. In such an embodiment, the first portion of the fluid collection assembly 101 is closer to the proximal surface 104 than the second portion while the second portion is closer to the distal surface 106 than the first portion. As such, when the tensioning element 116 is closer to the proximal surface 104, switching the tensioning element 116 from the relaxed state to a tensioned state causes the fluid collection assembly 101 to bend towards the proximal surface 104. Referring to FIGS. 1A and 1B, when the tensioning element 116 is closer to the proximal surface 104, the tensioning element 116 is in a relaxed state when the fluid collection assembly 101 exhibits the first shape (FIG. 1A) and in a tensioned state when the fluid collection assembly 101 exhibits the second shape (FIG. 1B). In an embodiment, not shown, the tensioning element 116 is positioned closer to the distal surface 106 than the proximal surface 104. In such an embodiment, the first portion of the fluid collection assembly 101 is closer to the distal surface 106 than the second portion while the second portion is closer to the proximal surface 104 than the first portion. As such, when the tensioning element 116 is closer to the distal surface, switching the tensioning element 116 from the relaxed state to a tensioned state causes the fluid collection assembly 101 to bend towards the distal surface 106. For instance, when the tensioning element 116 is positioned closer to the distal surface 106, the fluid collection assembly 101 may exhibit a first shape that is curved when the tensioning element 116 is in a relaxed state with the proximal surface 104 thereof forming a concave surface. Switching the tensioning element 116 to the tensioned state thereof may straighten the fluid collection assembly 101 (e.g., the second state may be a generally straight shape).

In an embodiment, as illustrated, a portion of the tensioning element 116 is configured to be disposed within the fluid impermeable barrier 102. In such an embodiment, the fluid impermeable barrier 102 may define at least one channel 118 configured to receive the tensioning element 116. The channel 118 may allow the fluid impermeable barrier 102 to insulate the tensioning element 116 from the bodily fluids that are received in the chamber 108. In an example, as illustrated, the channel 118 may extend along substantially all (e.g., greater than 80%) of a length of the fluid impermeable barrier 102. In such an example, the channel 118 may define an inlet 120 at or near a proximal end region 122 of the fluid impermeable barrier 102. The channel 118 may extend from the inlet 120 to or near a distal end region 124. Thus, the tensioning element 116 extends along all or substantially all of the length of the fluid impermeable barrier 102 thereby allowing the tensioning element 116 to affect the shape of the fluid collection assembly 101 along substantially all of the length thereof. In an example, the channel 118 may extend through only a portion (e.g., less than 80%, such as less than 65%, less than 50%, or less than 35%) of a length of the fluid impermeable barrier 102. In such an example, the tensioning element 116 may affect the shape of the fluid collection assembly 101 along only the portion of the length thereof. It is noted that at least a portion of the tensioning element 116 may not disposed in the fluid impermeable barrier 102, as will be discussed in more detail with regards to FIGS. 2A-2E.

In an embodiment, the at least one tensioning element 116 includes a plurality of tensioning elements. In such an embodiment, the fluid impermeable barrier 102 defines a plurality of channels that are configured to receive at least a portion of a corresponding one of the plurality of tensioning elements. The tensioning element 116 may include a plurality of tensioning elements for a variety of reasons. In an example, as will be discussed in more detail with regards to FIG. 3, the plurality of tensioning elements may allow for greater control of the shape of the fluid collection assembly 101. In an example, the plurality of tensioning elements may, collectively, increase the strength of the tensioning element 116 and/or may allow the tensioning element 116 to operate even when one of the plurality of tensioning elements fail or the fixed portion thereof becomes detached. In an example, as illustrated, the plurality of tensioning elements may allow the tensioning element 116 to avoid obstacles, such as the opening 110. For instance, the tensioning element 116 is positioned at the proximal end region 122 and the distal end region 124 such that, if the tensioning element 116 only included a single tensioning element 116, the tensioning element 116 would pass across the opening 110 or would have to deviate to one side of the opening 110. Passing the tensioning element 116 across the opening 110 may cause the tensioning element 116 to contact the individual which may cause discomfort. Further, deviating the tensioning element 116 to one side of the opening 110 may cause the fluid collection assembly 101 to bend to the side when the tensioning element 116 switches between the relaxed and tensioned states. However, selecting the tensioning element 116 to include a plurality of tensioning elements may allow the tensioning element 116 to avoid the opening 110 while preventing the fluid collection assembly 101 from bending to the side when switching the tensioning element 116 between the relaxed and tensioned states thereof. For instance, as best shown in FIGS. 1C and 1D, the at least one tensioning element 116 may include a first tensioning element 116a and a second tensioning element 116b and the at least one channel 118 may include a first channel 118a and a second channel 118b configured to receive the first tensioning element 116a and the second tensioning element 116b, respectively. The first channel 118a may extend along one side of the opening 110 when the second channel 118b extends along the opposing side of the opening 110 thus preventing the first and second tensioning elements 116a, 116b from extending across the opening 110. Further, applying a tensile force to both the first and second tensioning elements 116a, 116b may prevent the fluid collection assembly 101 from bending to either the side.

The fluid collection assembly 101 may exhibit any suitable shape when the fluid collection assembly 101 exhibits the first shape (FIG. 1A) and the second shape (FIG. 1B). In an example, as illustrated, the fluid collection assembly 101 exhibits a generally straight shape when the fluid collection assembly 101 exhibits the first shape and a generally curved shape when the fluid collection assembly 101 exhibits the second shape. As used herein, a generally curved shape may refer to a portion of an arc of a generally circular shape, a generally oval shape, a generally ellipsoid shape, a generally parabolic shape, any other curved shape, or combinations thereof. In an example, the fluid collection assembly 101 exhibits a generally curved shape when the fluid collection assembly 101 exhibits the first shape and a generally straight shape when the fluid collection assembly exhibits the second shape. In an example, the fluid collection assembly 101 may exhibit a first generally curved shape when the fluid collection assembly 101 exhibits the first shape and a second generally curved shape when the fluid collection assembly 101 exhibits the second shape. In such an example, the first and second generally curved shapes are different. For instance, the first shape may exhibit an average radius of curvature that is greater than or less than the average radius of curvature of the second shape and/or the first shape may be an arc of a different curved shape than the second shape.

As previously discussed, the fluid collection assembly 101 may exhibit the first shape when the tensioning element 116 is in the relaxed state and the second shape when the tensioning element 116 is in the tensioned state. It is also noted that the shape of the fluid collection assembly 101 may vary depending on the magnitude of the tensile force that is applied to the tensioning element 116. For example, the fluid collection assembly 101 may exhibit a first shape when the tensioning element 116 is in a relaxed state, a second shape when the tensioning element 116 has a first tensile force applied thereto, and a third shape when the tensioning element 116 has a second tensile force applied thereto that is different in magnitude than the first tensile force. The first, second, and third shapes of the fluid collection assembly 101 are each different. When the second tensile force is less than the first tensile force, the third shape of the fluid collection assembly 101 may be more similar to the first shape than the second shape. When the second tensile force is greater than the first tensile force, the second shape of the fluid collection assembly 101 may be more similar to the first shape than the third shape.

The fluid collection system 100 may include at least one locking device 132. The locking device 132 is configured to receive the tensioning element 116. The locking device 132 is also configured to at least one of apply the tensile force to the tensioning element 116 or maintain the application of the tensile force to the tensioning element 116. The locking device 132 may include, for example, a ratchet-type device (FIG. 4A), a sliding device that moves along a component of the fluid collection system 100 (FIG. 34), tape (FIG. 4C), a spring, clamp, a hook the tensioning element 116 may be tied to, or any other device configured to at least one of apply or maintain the tensile force to the tensioning element 116. To facilitate the operation of the locking device 132, the locking device 132 exhibits a fixed position relative to the fluid collection assembly 101. For example, the locking device 132 may be unable to consistently apply and/or maintain the tensile force on the tensioning element 116 if, in response to the tensile force, the locking device 132 moves closer to the fluid collection assembly 101 and/or vice versa.

The locking device 132 may have any suitable location relative to the fluid collection assembly 101. The locking device 132 may be located near the inlet 120 to minimize a length of the tensioning element 116. In an example, as illustrated, the locking device 132 may be located on the conduit 128 at or near the fluid outlet 112 since (as illustrated) the inlet 120 is near the inlet 120 and the conduit 128 may exhibit sufficient rigidity to prevent the locking device 132 moving closer to the fluid collection assembly 101 when a tensile force is applied to the tensioning element 116. In an example, the locking device 132 may be located on the fluid impermeable barrier 102 at or near the inlet 120. In an example, the locking device 132 may be at least partially disposed in the fluid collection assembly 101, such as at least partially disposed in the chamber 108. In an example, the locking device 132 may be disposed on the patient using the fluid collection assembly 101 or on an item of furniture adjacent to the individual (e.g., a bed, a nightstand, a chair, a vacuum source, a fluid storage container, etc.).

As previously discussed, the fluid collection assembly 101 includes a fluid impermeable barrier 102. The fluid impermeable barrier 102 may be formed of any suitable fluid imporous material(s), such as a fluid impermeable polymer (e.g., silicone, polypropylene, polyethylene, polyethylene terephthalate, neoprene, a polycarbonate, etc.), a metal film, natural rubber, another suitable material, or combinations thereof. The fluid impermeable barrier 102 substantially prevents the bodily fluids from passing through the fluid impermeable barrier 102. In an example, the fluid impermeable barrier 102 may be air permeable and fluid impermeable. In such an example, the fluid impermeable barrier 102 may be formed of a hydrophobic material that defines a plurality of pores. At least a surface of the fluid impermeable barrier 102 that may contact the patient may be formed from a soft and/or smooth material (e.g., silicone), thereby reducing chaffing. In an embodiment, the fluid impermeable barrier 102 may be formed from a flexible material, such as silicone, which allows the fluid impermeable barrier 102 to be bent into a shape that conforms the anatomy of the patient. Further, as shown in FIGS. 1A and 1B, forming the fluid impermeable barrier 102 from a flexible material allows the fluid impermeable barrier 102 to accommodate the shape and/or size causes by switching the tensioning element 116 between the relaxed and tensioned states thereof.

In some examples, the fluid impermeable barrier 102 may be tubular (ignoring the opening 110), such as substantially cylindrical (as shown), oblong, prismatic, or flattened tubes. During use, the outer surface (e.g., at least a portion of one or more of the proximal surface 104, the distal surface 106, or the lateral surface 130) of the fluid impermeable barrier 102 may contact the patient. The fluid impermeable barrier 102 may be sized and shaped to fit in the gluteal cleft between the legs of a female user.

The opening 110 provides an ingress route for fluids to enter the chamber 108. The opening 110 may be defined by the proximal surface 104 of the fluid impermeable barrier 102. For example, the opening 110 is formed in and extends through the fluid impermeable barrier 102, from the proximal surface 104 to an inner surface 134 of the fluid impermeable barrier 102, thereby enabling bodily fluids to enter the chamber 108 from outside of the fluid collection assembly 101. The opening 110 may be an elongated hole in the fluid impermeable barrier 102. For example, the opening 110 may be defined as a cut-out in the fluid impermeable barrier 102. The opening 110 may be located and shaped to be positioned adjacent to a female urethral opening.

The fluid collection assembly 101 may be positioned proximate to the female urethral opening and urine or other bodily fluids may enter the chamber 108 of the fluid collection assembly 101 via the opening 110. The fluid collection assembly 101 is configured to receive the bodily fluids into the chamber 108 via the opening 110. When in use, the opening 110 may have an elongated shape that extends from a first location below the urethral opening (e.g., at or near the anus or the vaginal opening) to a second location above the urethral opening (e.g., at or near the top of the vaginal opening or the mons pubis).

The opening 110 may have an elongated shape because the space between the legs of a female is relatively small when the legs of the female are closed, thereby only permitting the flow of the bodily fluids along a path that corresponds to the elongated shape of the opening 110 (e.g., longitudinally extending opening). The opening 110 in the fluid impermeable barrier 102 may exhibit a length measured along the longitudinal axis of the fluid collection assembly 101 that may be at least about 10% of the length of the fluid collection assembly 101, such as about 25% to about 50%, about 40% to about 60%, about 50% to about 75%, about 65% to about 85%, or about 75% to about 95% of the length of the fluid collection assembly 101.

The opening 110 in the fluid impermeable barrier 102 may exhibit a width measured transverse to the longitudinal axis of the fluid collection assembly 101 that may be at least about 10% of the circumference of the fluid collection assembly 101, such as about 25% to about 50%, about 40% to about 60%, about 50% to about 75%, about 65% to about 85%, or about 75% to about 100% of the circumference of the fluid collection assembly 101. The opening 110 may exhibit a width that is greater than 50% of the circumference of the fluid collection assembly 101 since the vacuum (e.g., suction) through the conduit 128 pulls the fluid through the porous material 114 and into the conduit 128.

In some examples, the opening 110 may be vertically oriented (e.g., having a major axis parallel to the longitudinal axis of the fluid collection assembly 101). In some examples (not shown), the opening 110 may be horizontally oriented (e.g., having a major axis perpendicular to the longitudinal axis of the fluid collection assembly 101). In an example, the fluid impermeable barrier 102 may be configured to be attached to the patient, such as adhesively attached (e.g., with a hydrogel adhesive) to the patient. According to an example, a suitable adhesive is a hydrogel layer.

As previously discussed, the fluid impermeable barrier 102 may define fluid outlet 112 configured to remove bodily fluids from the chamber 108. The fluid outlet 112 is distinct from the opening 110. In some examples, the fluid outlet 112 is sized to receive the conduit 128. The conduit 128 may be disposed in the chamber 108 via the fluid outlet 112. The fluid outlet 112 may be sized and shaped to form an at least substantially fluid tight seal against the conduit 128 or the at least one tube substantially preventing the bodily fluids from escaping the chamber 108.

The fluid impermeable barrier 102 may include markings thereon, such as one or more markings to aid a user in aligning the fluid collection assembly 101 on the patient. For example, a line on the fluid impermeable barrier 102 (e.g., opposite the opening 110) may allow a healthcare professional to align the opening 110 over the urethral opening of the patient. In examples, the markings may include one or more of alignment guide or an orientation indicator, such as a stripe or hashes. Such markings may be positioned to align the fluid collection assembly 101 to one or more anatomical features such as a pubic bone, etc.

As previously discussed, the fluid collection assembly 101 includes porous material 114 disposed in the chamber 108. The porous material 114 may cover at least a portion (e.g., all) of the opening 110. The porous material 114 is exposed to the environment outside of the chamber 108 through the opening 110. The permeable properties referred to herein may be wicking, capillary action, absorption, diffusion, or other similar properties or processes, and are referred to herein as "permeable" and/or "porous." The porous material 114 may also wick the bodily fluids generally towards an interior of the chamber 108, as discussed in more detail below. The porous material 114 may include one or more of a fluid permeable membrane 136 or a fluid permeable support 138.

In an embodiment, at least a portion of the porous material 114 may be a wicking material configured to wick the bodily fluids away from the opening 110, thereby preventing bodily fluids from escaping the chamber 108. The wicking material may not include absorption of the bodily fluids into the wicking material. Put another way, substantially no absorption of the bodily fluids into the wicking material may take place after the wicking material is exposed to the bodily fluids. While no absorption is desired, the term "substantially no absorption" may allow for nominal amounts of absorption of the bodily fluids into the wicking material (e.g., absorbency), such as about 30 wt % of the dry weight of the wicking material, about 20 wt %, about 15 wt %, about 10 wt %, about 7 wt %, about 5 wt %, about 3 wt %, about 2 wt %, about 1 wt %, or about 0.5 wt % of the dry weight of the wicking material. In an embodiment, the porous material 114 may be at least one of an absorbent material or adsorbent material instead of or in addition to being a wicking material.

The fluid collection assembly 101 may include the fluid permeable membrane 136 disposed in the chamber 108. The fluid permeable membrane 136 may cover at least a portion (e.g., all) of the opening 110. The fluid permeable membrane 136 may be composed to pull/push the bodily fluids away from the opening 110, thereby promoting fluid flow into the chamber 108, prevent fluid remaining on the vulva of the patient, and preventing the bodily fluids from escaping the chamber 108.

The fluid permeable membrane 136 may include any material that may be permeable to the bodily fluids. For example, the fluid permeable membrane 136 may include fabric, such as a gauze (e.g., a silk, linen, or cotton gauze), another soft fabric, or another smooth fabric. Forming the fluid permeable membrane 136 from gauze, soft fabric, and/or smooth fabric may reduce chaffing caused by the fluid collection assembly 101 and makes wearing the fluid collection assembly more comfortable. In an embodiment, the fluid permeable membrane 136 may define a plurality of perforations or may be continuous (e.g., does not define perforations).

The fluid collection assembly 101 may include the fluid permeable support 138 disposed in the chamber 108. The fluid permeable support 138 is configured to support the fluid permeable membrane 136 and maintain the shape of the chamber 108 since the fluid impermeable barrier 102 and the fluid permeable membrane 136 may be formed from a relatively foldable, flimsy, or otherwise easily deformable material. For example, the fluid permeable support 138 may be positioned so the fluid permeable membrane 136 is disposed between the fluid permeable support 138 and the fluid impermeable barrier 102. The fluid permeable support 138 may support and maintain the position of the fluid permeable membrane 136 and the shape of the chamber 108. The fluid permeable support 138 may include any material that may be permeable to the bodily fluids, such as any of the fluid permeable membrane 136 materials disclosed above. For example, the fluid permeable membrane 136 material(s) may be utilized in a more dense or rigid form than in the fluid permeable membrane 136 when used as the fluid permeable support 138. The fluid permeable support 138 may be formed from any fluid porous material that is less deformable than the fluid permeable membrane 136. For example, the fluid permeable support 138 may include a porous polymer (e.g., nylon, polyester, polyurethane, polyethylene, polypropylene, etc.) structure (e.g., spun fibers such as spun nylon fibers) or a foam (e.g., an open cell foam). In some examples, the fluid permeable support 138 may be formed from a natural material, such as cotton, wool, silk, or combinations thereof. In such examples, the material may have a coating to prevent or limit absorption of the bodily fluids into the material, such as a water repellent coating. In some examples, the fluid permeable support 138 may be formed from fabric, felt, gauze, or combinations thereof.

In some examples, the fluid permeable membrane 136 may be omitted. For example, the porous material 114 may include only the fluid permeable support 138. In some examples, the fluid permeable support 138 may be optionally omitted from the fluid collection assembly 101 and the porous material 114 may only include the fluid permeable membrane 136.

In an embodiment, the fluid permeable membrane 136 and/or the fluid permeable support 138 are wicking materials. In such an embodiment, the fluid permeable support 138 may have a greater ability to wick the bodily fluids than the fluid permeable membrane 136. In some examples, the wicking ability of the fluid permeable support 138 and the fluid permeable membrane 136 may be substantially the same. In an embodiment, the fluid permeable membrane 136 and/or the fluid permeable support 138 are non-wicking materials (e.g., absorbent and/or adsorbent materials).

In an embodiment, not shown, the fluid permeable membrane 136 and the fluid permeable support 138 may at least substantially completely fill the portions of the chamber 108 not occupied by the conduit 128. In an embodiment, as shown in FIG. 1D, the fluid permeable membrane 136 and the fluid permeable support 138 may not substantially completely fill the portions of the chamber 108 not occupied by the conduit 128. In such an embodiment, the fluid collection assembly 101 includes the fluid reservoir 140 disposed in the chamber 108.

The fluid reservoir 140 is a substantially unoccupied portion of the chamber 108. The fluid reservoir 140 may be defined between at least the fluid impermeable barrier 102 and at least one of the fluid permeable membrane 136 or the fluid permeable support 138. The bodily fluids in the chamber 108 may flow through the fluid permeable membrane 136 and/or fluid permeable support 138 to the fluid reservoir 140. The fluid reservoir 140 may retain of the bodily fluids. The bodily fluids in the chamber 108 may flow through the fluid permeable membrane 136 and/or fluid permeable support 138 and, optionally, to the fluid reservoir 140. The fluid impermeable barrier 102 may retain the bodily fluids in the fluid reservoir 140. The fluid reservoir 140 may be in a portion of the chamber 108 designed to be in a gravimetrically low point of the fluid collection assembly 101 when the fluid collection assembly 101 is worn.

The fluid collection systems disclosed herein may include the tensioning elements positioned in locations of the fluid collection assembly other than disposing the tensioning elements within the fluid impermeable barrier. FIGS. 2A-2E are cross-sectional schematics of fluid collection systems having at least one tensioning element positioned at different locations of the fluid collection assembly, according to different embodiments. Except as otherwise disclosed herein, the fluid collection systems illustrated in FIGS. 2A-2E are the same or substantially similar to any of the fluid collection systems disclosed herein. For example, the fluid collection systems includes a fluid collection assembly and at least one tensioning element at least partially disposed in the fluid collection assembly. The fluid collection assembly includes a fluid impermeable at least barrier defining a chamber, at least one opening, and a fluid outlet. The fluid collection assembly also includes at least one porous material disposed in the chamber.

Referring to FIG. 2A, the fluid collection system 200a includes a fluid collection assembly 201a and at least one tensioning element 216a. The fluid collection assembly 201a includes a fluid impermeable barrier 202a defining a chamber 208a and at least one porous material 214a disposed in the chamber 208a. At least a portion of the tensioning element 216a is positioned between the fluid impermeable barrier 202a and the porous material 214a. Thus, the fluid impermeable barrier 202a may separate the tensioning element 216a from the patient which may make the fluid collection system 200a more comfortable to use than if the tensioning element 216s contacted the patient.

Similar to any of the fluid collection systems disclosed herein, the at least one tensioning element 216a may include a plurality of tensioning elements, such as a first tensioning element 216a' and a second tensioning element 216a". The first tensioning element 216a' may be positioned to one side of the opening 210a while the second tensioning element 216a" may be positioned on the other side of the opening 210a. Thus, similar to the first and second tensioning elements 116a, 116b of FIGS. 1C and 1D, the first and second tensioning elements 216a', 216a" may not extend across the opening 210a.

In an embodiment, the fluid collection assembly 201a may include one or more braces 242a. The braces 242a are attached to and extend between at least a portion of the tensioning element 216a and at least a portion of the fluid impermeable barrier 202a or the porous material 214a. The braces 242a may prevent the tensioning element 216a from moving from a location between the fluid impermeable barrier 202a and the porous material 214a to a location that allows the tensioning element 216a to extend across the opening 210a. In an example, the braces 242a may be strands (e.g., wires, strips of material, etc.) that extend from and are fixedly attached to at least a portion of the tensioning element 216a and at least one of the fluid impermeable barrier 202a or the porous material 210a. In such an example, the braces 242a may be elastic, thereby allowing the braces 242a to stretch when the tensioning element 216a switches between the relaxed and tensioned states thereof. In an example, the braces 242a may loop around tensioning element 216a forming a generally U-shape (e.g., the fluid impermeable barrier 202a or the porous material 210a is attached to the terminal ends of and closes the opening of the U-shape), a generally P-shape, or O-shape. The U-, P-, or O-shape of the braces 242a may form a passageway in which a portion of the tensioning element 216a may be disposed. The passageway may be configured to allow the tensioning element 216a to move therein, such as move therein when the tensioning element 216a switches between the relaxed and tensioned states thereof. The braces 242a may be formed from fabric, one or more metals, one or more polymers, or combinations thereof.

Referring to FIG. 2B, the fluid collection system 200b includes a fluid collection assembly 201b and at least one tensioning element 216b. The fluid collection assembly 201b includes a fluid impermeable barrier 202b and at least one porous material 214b. At least a portion of the tensioning element 216b is positioned in the fluid collection assembly 201b to be within the porous material 214b. For example, the porous material 214b may include a fluid permeable membrane 236b and a fluid permeable support 238b. In such an example, the tensioning element 216b may be positioned between the fluid permeable membrane 236b and the fluid permeable support 238b. The tensioning element 216b may be positioned within the porous material 214b, for example, using a dual extrusion technique or threading the tensioning element 216b between the fluid permeable membrane 236b and the fluid permeable support 238b.

In an embodiment, as illustrated, that tensioning element 216b may extend directly beneath the opening 210b since the tensioning element 216b is spaced from the opening 210b by a portion of the porous material 214b (e.g., the fluid permeable membrane 236b prevents the tensioning element 216b from contacting the individual). In an embodiment, the tensioning element 216b may include a plurality of tensioning elements.

Referring to FIG. 2C, the fluid collection system 200c includes a fluid collection assembly 201c and at least one tensioning element 216c. The fluid collection assembly 201c includes a fluid impermeable barrier 202c, at least one porous material 214c, and a conduit 228c. At least a portion of the tensioning element 216c is positioned in the fluid collection assembly 201c to be between the porous material 214c and the conduit 228c. In an embodiment, as illustrated, that tensioning element 216c may extend directly beneath the opening 210c since the tensioning element 216c is spaced from the opening 210c by the porous material 214c. In an embodiment, the tensioning element 216c may include a plurality of tensioning elements.

Referring to FIG. 2D, the fluid collection system 200d includes a fluid collection assembly 201d and at least one tensioning element 216d. The fluid collection assembly 201d includes a fluid impermeable barrier 202d, at least one porous material 214d, and a conduit 228d. At least a portion of the tensioning element 216d is positioned in the fluid collection assembly 201d to be within the conduit 228d. The walls of the conduit 228d may define at least one channel therein. The tensioning element 216d may be disposed within the channels. The tensioning element 216d may be disposed in the channel, for example, using a dual extrusion technique. In an embodiment, as illustrated, that tensioning element 216d may extend directly beneath the opening 210d since the tensioning element 216d is spaced from the opening 210d by the porous material 214d. In an embodiment, the tensioning element 216d may include a plurality of tensioning elements.

Referring to FIG. 2E, the fluid collection system 200e includes a fluid collection assembly 201e and at least one tensioning element 216e. The fluid collection assembly 201e includes a fluid impermeable barrier 202e, at least one porous material 214e, and a conduit 228e. At least a portion of the tensioning element 216e is positioned in the fluid collection assembly 201e to be within a passageways 244e defined by the conduit 228e.

It is noted that any of the fluid collection systems may include at least one tensioning elements that is positioned in two or more of the locations of the fluid collection assembly disclosed herein. In an example, at least two of a portion of the tensioning element may be disposed in the fluid impermeable barrier (as shown in FIGS. 1C and 1D), a portion of the tensioning element may be positioned between the fluid impermeable barrier and the porous material, within the porous material, between the conduit and the porous material, within a channel defined by the conduit, or with a passageway defined by the conduit. In an example, the at least one tensioning element may include a plurality of tensioning elements and at least two of the tensioning elements are positioned in different locations of the fluid collection assembly.

Figure 3:
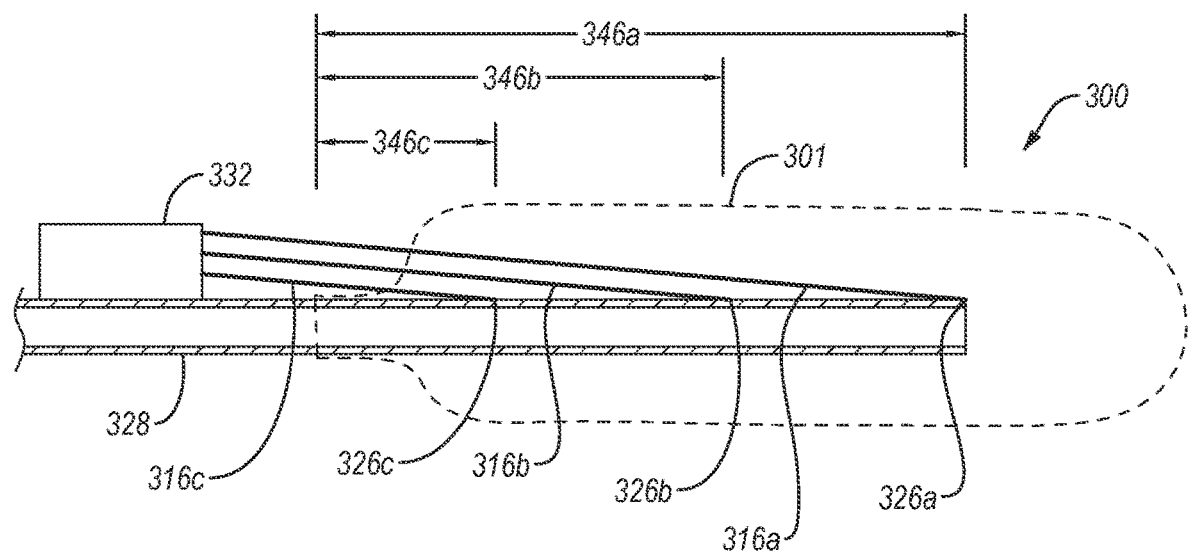
FIG. 3 is a schematic cross-sectional schematic of a fluid collection system, according to an embodiment.

As previously discussed, the fluid collection systems disclosed herein may include a plurality of tensioning elements. However, the plurality of tensioning elements may be configured to control the shape of different portions of the fluid collection assembly. For example, FIG. 3 is a cross-sectional schematics of a fluid collection system 300, according to an embodiment. Except as otherwise disclosed herein, the fluid collection system 300 is the same or substantially similar to any of the fluid collection systems disclosed herein. For example, the fluid collection system includes a fluid collection assembly 301, a plurality of tensioning elements, a conduit 328, and at least one locking device 332. The fluid collection assembly 301 may include a fluid impermeable barrier and a porous material, as previously discussed herein. For illustrative purposes, the individual components of the fluid collection assembly 301 are not illustrated and the exterior of the fluid collection assembly 301 is illustrated using dashed lines.

As previously discussed, the fluid collection assembly 301 includes a plurality of tensioning elements. In the illustrated embodiment, the fluid collection assembly 301 is illustrated as including a first tensioning element 316a, a second tensioning element 316b, and a third tensioning element 316c. However, it is noted that the fluid collection assembly 301 may include only two tensioning elements or four or more tensioning elements and that the same principles discussed herein apply regardless of the number of tensioning elements.

Each of the first, second, and third tensioning elements 316a, 316b, 316c include fixed portions 326a, 326b, 326c, respectively, that are connected to different portion of the fluid collection assembly 301. In the illustrated embodiment, the first, second, and third fixed portions 326a, 326b, 326c are attached to the conduit 328. However, as previously discussed, the fixed portions 326a, 326b, 326c may be attached to other components of the fluid collection assembly 301, such as the fluid impermeable barrier or the porous material. The first fixed portion 326a is attached to a first location of the fluid collection assembly 301, the second fixed portion 326b is attached to a second location of the fluid collection assembly 301 that is closer to the locking device 332 than the first location, and the second fixed portion 326c is attached to a third location of the fluid collection assembly 301 that is closer to the locking device 332 than the first and second locations.

The first tensioning element 316a is configured to change the shape of a first region 346a of the fluid collection assembly 301 that extends generally between the first location and an inlet (e.g., inlet 120 of FIGS. 1A, 1B, and 1D) through which the first tensioning element 316a enters the fluid collection assembly 301. The second tensioning element 316b is configured to change the shape of a second region 346b of the fluid collection assembly 301 that generally extends between the second location and an inlet through which the second tensioning element 316b enters the fluid collection assembly 301. The third tensioning element 316c is configured to change the shape of a third region 346c of the fluid collection assembly 301 that generally extends between the third location and an inlet through which the third tensioning element 316c enters the fluid collection assembly 301. It is noted that the first, second, and third portions 346a, 346b, 346c of the fluid collection assembly overlap and that the inlet through which the first, second, and third tensioning elements 316a, 316b, 316c enter the fluid collection assembly 301 may be the same inlet or different inlets.

The fluid collection assembly 301 may exhibit a first shape when each of the first, second, and third tensioning elements 316a, 316b, 316c are in a relaxed shape. The shape of the fluid collection assembly 301 may be controlled by selectively switching one or more of the first, second, and third tensioning elements 316a, 316b, 316c to the tensioned states thereof and varying the magnitude of the tensile force applied thereto. In an embodiment, the fluid collection assembly 301 is switched from a first shape to a second shape by switching the first tensioning element 316a from a relaxed state to a tensioned state thereof. The second shape includes modifying the shape of the first region 346a of the fluid collection assembly 301. The shape of the fluid collection assembly 301 may be further changed by selectively switching one or more of the second or third tensioning elements 316b, 316c to the tensioned states thereof. In an example, the fluid collection assembly 301 may be switched from the second shape to a third shape by switching the second tensioning element 316b to the tensioned state thereof which changes the shape of the second region 346b of the fluid collection assembly 301 but may not change the shape of the portion of the first region 346a that does not overlap the second region 346b. In an example, the fluid collection assembly 301 may be switched from the second shape or the third shape to a fourth shape by switching the third tensioning element 316c to the tensioned state thereof which changes the shape of the third region 346c of the fluid collection assembly 301 but may not change the shape of the portions of the first region 346a and second region 346b that do not overlap the third region 346c. In an embodiment, the fluid collection assembly 301 is switched from the first shape to a fifth shape by switching the second tensioning element 316b from a relaxed state to a tensioned state thereof. The fifth shape includes modifying the shape of the second region 346b of the fluid collection assembly 301 but may not affect the portions of the first region 346a that does not overlap with the second region 346b. The fluid collection assembly 301 may be switched from the fifth shape to a sixth shape by switching the third tensioning element 316c from a relaxed state to a tensioned state thereof which changes the shape of the third region 346c of the fluid collection assembly 301 but may not changes the shape of the portions of the first region 346a and the second region 346c that do not overlap the second region 346c. In an embodiment, the fluid collection assembly 301 may switch from the first state to a seventh shape by switching third tensioning element 316c to the tensioned state thereof. In such an embodiment, the third tensioning element 316c changes the shape of the third region 346c but may not substantially change the shape of the portions of the first region 346a and the second region 346b that do not overlap with the third region 346c. It is noted that these embodiments are examples provided for illustrative purposes only and should not be construed as limiting the operation of the fluid collection system 300. Further, it is noted that the first, second, and/or third tensioning elements 316a, 316b, 316c may be switched from their respective relaxed states to their respective tensioned states in different orders than provided above, without limitation, and still obtain the same or substantially the same result. For example, the fluid collection assembly 301 may switch from the first shape to the third shape by switching one or more of the second tensioning element 316b or the third tensioning element 316c to the tensioned state thereof before or substantially simultaneously with switching the first tensioning element 316a to the tensioned state thereof.

Figure 4A:
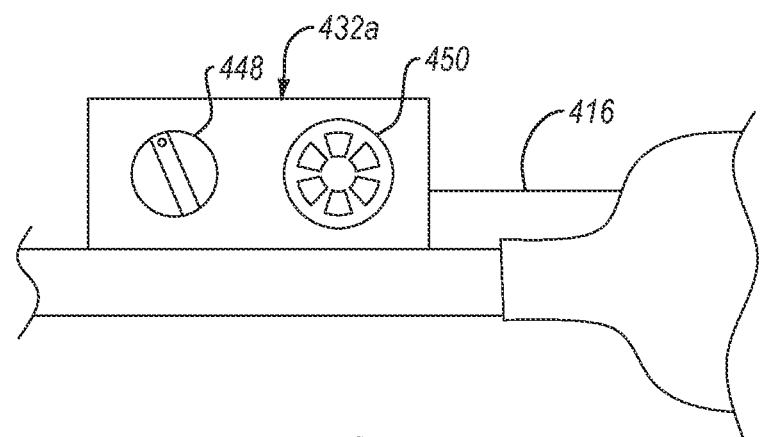
FIGS. 4A-4C are isometric views of different locking devices that may be used in any of the fluid collection systems disclosed herein, according to different embodiments.
Figure 4B:
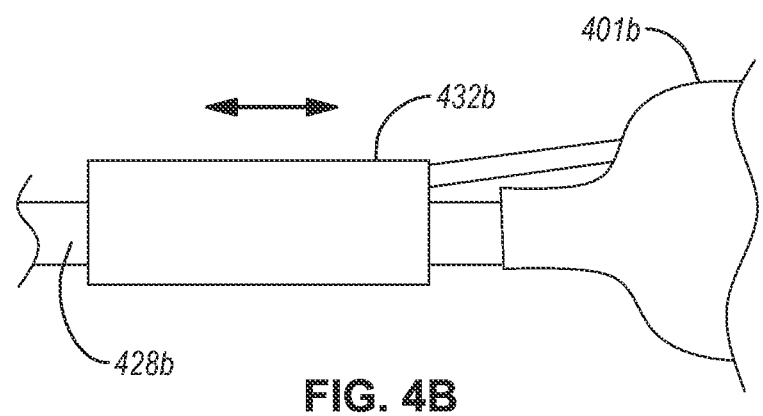
Figure 4C:
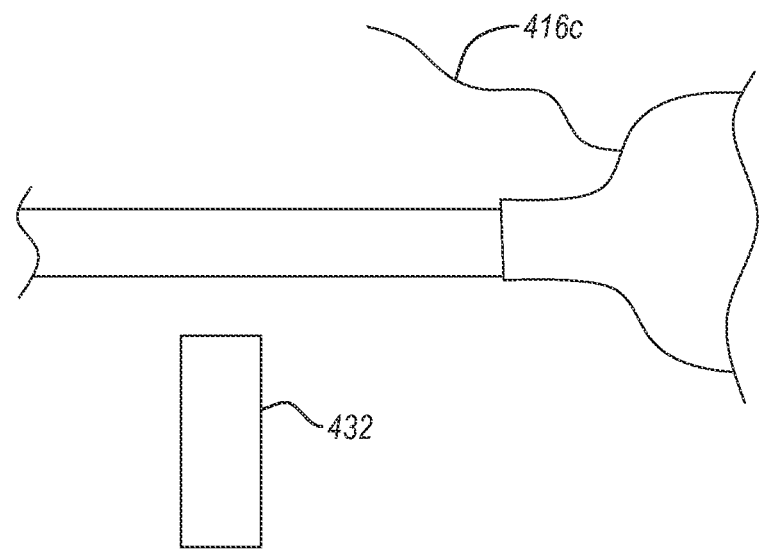

As previously indicated, FIGS. 4A-4C are isometric views of different locking devices that may be used in any of the fluid collection systems disclosed herein, according to different embodiments. Referring to FIG. 4A, the locking device 432a is a ratchet-type locking device. For example, the locking device 432a is configured to selectively allow the tensioning element 416a to be drawn into the locking device 432a and/or selectively allow the tensioning element 416a to be withdrawn from the locking device 432a. In other words, the locking device 432a may be configured to restrict the movement of the tensioning element 416a to one direction, either into or out of the locking device 432a.

The locking device 432a may include a first actuator 448 that is configured to allow a user to select whether the locking device 432a allows the tensioning element 416a to be drawn into the locking device 432a and/or allows the tensioning element 416a to be withdrawn from the locking device 432a. For example, the first actuator 448 may be configured to switch from a first state to a second state, wherein the first actuator 448 allow the locking device 432a to draw the tensioning element 416a into the locking device when the first actuator 448 is in the first state and to withdraw the tensioning element 416a from the locking device when the first actuator 448 is in the second state. The locking device 432a may also include a second actuator 450 that allows a user to draw the tensioning element 416a into the locking device 432a and/or out of the locking device 432a. The first and second actuators 448, 450 may include any suitable actuators. For example, in the illustrated embodiment, the first and second actuators 448, 450 are a lever (e.g., switch) and a knob, respectively. Alternatively, one or more of the first or second actuators 448, 450 may include button(s), handle(s), or any other actuator(s).

In a particular example, the locking device 432a may include a spool (not shown, in interior) that is configured to receive the tensioning element 416a. The first actuator 448 may be configured to restrict rotation of the spool to a single direction. For instance, the first actuator 448 may only allow the spool to rotate in a direction that pulls the tensioning element 416a onto the spool when the first actuator 448 is in a first state. Further, the first actuator 448 may only allow the spool to rotate in a direction that allows the tensioning element 416a to leave the spool when the first actuator 448 is in a second state. The second actuator 450 is connected to the spool and is configured to rotate the spool.

Referring to FIG. 4B, the locking device 432b is a sliding-type locking device. The locking device 432b defines a passageway (not shown, obscured) that is configured to receive the conduit 428b. The kinetic friction between the surface of the locking device 432b that defines the passageway and the conduit 428b maintains the position of the locking device 432b on the conduit 428b, even when the locking device 432b applies a tensile force to the tensioning element 416b, up to a threshold magnitude. However, manipulation of the locking device 432b by a user may be sufficient to overcome kinetic friction between the surface of the locking device 432b that defines the passageway and the conduit 428b. For example, the user may switch the tensioning element 416b from a relaxed state to a tensioned state or increase a magnitude of a tensile force applied to the tensioning element 416b by moving the locking device 432b away from the fluid collection assembly 401b. Further, the user may switch the tensioning element 416b from a tensioned state to a relaxed state or decrease a magnitude of a tensile force applied to the tensioning element 416b by moving the locking device 432b towards the fluid collection assembly 401b.

Referring to FIG. 4C, the locking device 432c is tape. A user may pull or release the tensioning element 416c to selectively switch the locking device 432c from a relaxed state to a tensioned state, a tensioned state to a relaxed state, or to control a magnitude of the tensile force applied to the tensioning element 416c. Once the user stops pulling or releasing the tensioning element 416c, the locking device 432c may be used to secure a position of the tensioning element 416c such that the state of the tensioning element 416c and/or the magnitude of the tensile force applied to the tensioning element 416c maintains unchanged. The locking device 432c may be removed if the user wants to further pull or release the tensioning element 416c.

As previously discussed, the fluid collection systems disclosed herein may include a plurality of tensioning element. In an embodiment, the fluid collection systems may include a plurality of locking devices. Each of the locking devices may receive at least one of the plurality of the tensioning elements. The plurality of locking devices may be the same or different. In an embodiment, the fluid collection systems may include a single locking device that receives each of the plurality of tensioning elements.

Figure 5:
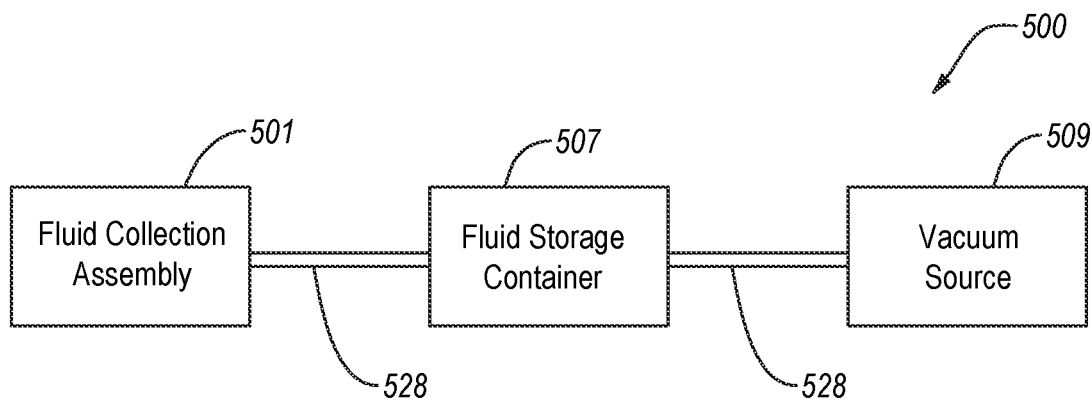
FIG. 5 is a block diagram of a system for fluid collection, according to an embodiment.

FIG. 5 is a block diagram of a system 500 for fluid collection, according to an embodiment. The system 500 includes a fluid collection assembly 501, a fluid storage container 507, and a vacuum source 509. The fluid collection assembly 501, the fluid storage container 507, and the vacuum source 509 may be fluidly coupled to each other via one or more conduits 528. For example, fluid collection assembly 501 may be operably coupled to one or more of the fluid storage container 507 or the vacuum source 509 via the conduit 528. Fluid (e.g., urine or other bodily fluids) collected in the fluid collection assembly 501 may be removed from the fluid collection assembly 501 via the conduit 528 which protrudes into the fluid collection assembly 501. For example, an inlet of the conduit 528 may extend into the fluid collection assembly 501, such as to a fluid reservoir therein. The outlet of the conduit 528 may extend into the fluid collection assembly 501 or the vacuum source 509. Suction force may be introduced into the chamber of the fluid collection assembly 501 via the inlet of the conduit 528 responsive to suction (e.g., vacuum) force applied at the outlet of the conduit 528.

The suction force may be applied to the outlet of the conduit 528 by the vacuum source 509 either directly or indirectly. The suction force may be applied indirectly via the fluid storage container 507. For example, the outlet of the conduit 528 may be disposed within the fluid storage container 507 and an additional conduit 528 may extend from the fluid storage container 507 to the vacuum source 509. Accordingly, the vacuum source 509 may apply suction to the fluid collection assembly 501 via the fluid storage container 507. The suction force may be applied directly via the vacuum source 509. For example, the outlet of the conduit 528 may be disposed within the vacuum source 509. An additional conduit 528 may extend from the vacuum source 509 to a point outside of the fluid collection assembly 501, such as to the fluid storage container 507. In such examples, the vacuum source 509 may be disposed between the fluid collection assembly 501 and the fluid storage container 507.

The fluid collection assembly 501 may be similar or identical to any of the fluid collection assemblies disclosed herein in one or more aspects. The fluid collection assembly 501 may be shaped and sized to be positioned adjacent to a female urethral opening. For example, the fluid collection assembly 501 may include a fluid impermeable barrier at least partially defining a chamber (e.g., interior region) of the fluid collection assembly 501. The fluid impermeable barrier also defines at least one opening extending therethrough from the external environment. The opening may be positioned adjacent to the female urethral opening. The fluid collection assembly 501 may include porous material disposed in the chamber, such as one or more of a fluid permeable support and a fluid permeable membrane. The system 500 may include at least one tensioning element (not shown) at least partially disposed in the fluid collection assembly 501. The conduit 528 may extend into the fluid collection assembly 501 at a first end (e.g., proximal) region, through one or more of the fluid impermeable barrier or the porous material to a second end region of the fluid collection assembly 501. The conduit 528 includes an inlet and an outlet, the outlet being fluidly coupled to the fluid storage container and the inlet being positioned in a portion of the chamber selected to be at a gravimetrically low point of the fluid collection assembly when worn.

The fluid storage container 507 is sized and shaped to retain a fluid therein. The fluid storage container 507 may include a bag (e.g., drainage bag), a bottle or cup (e.g., collection jar), or any other enclosed container for storing bodily fluid(s) such as urine. In some examples, the conduit 528 may extend from the fluid collection assembly 501 and attach to the fluid storage container 507 at a first point therein. An additional conduit 528 may attach to the fluid storage container 507 at a second point thereon and may extend and attach to the vacuum source 509. Accordingly, a vacuum (e.g., suction) may be drawn through fluid collection assembly 501 via the fluid storage container 507. Fluid, such as urine, may be drained from the fluid collection assembly 501 using the vacuum source 509.

The vacuum source 509 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 509 may provide a vacuum or suction to remove fluid from the fluid collection assembly 501. In some examples, the vacuum source 509 may be powered by one or more of a power cord (e.g., connected to a power socket), one or more batteries, or even manual power (e.g., a hand operated vacuum pump). In some examples, the vacuum source 509 may be sized and shaped to fit outside of, on, or within the fluid collection assembly 501. For example, the vacuum source 509 may include one or more miniaturized pumps or one or more micro pumps. The vacuum sources 509 disclosed herein may include one or more of a switch, a button, a plug, a remote, or any other device suitable to activate the vacuum source 509.

Figure 6:
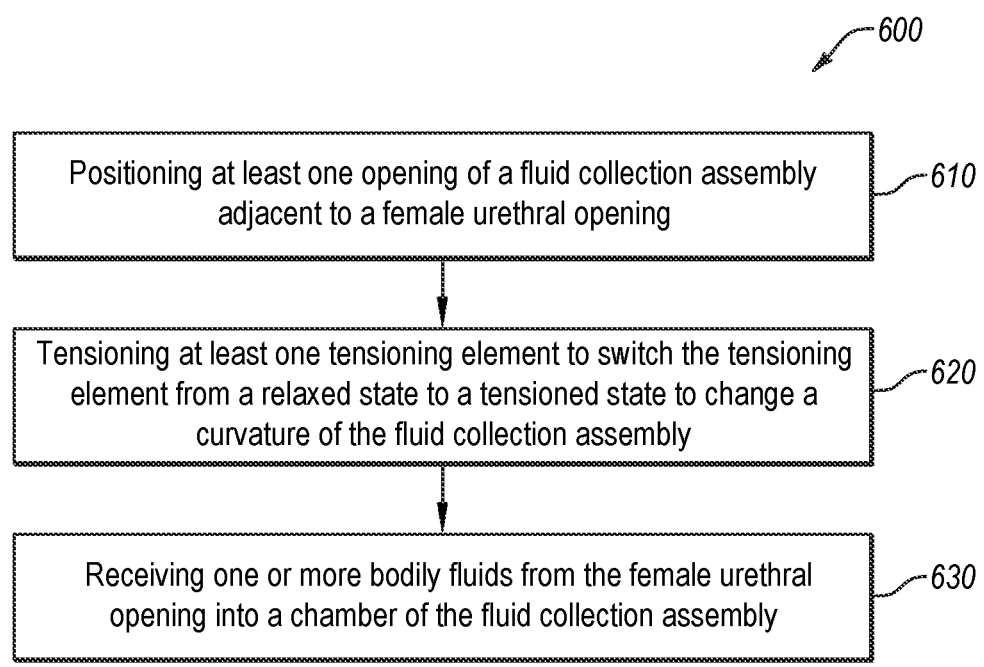
FIG. 6 is a flow diagram of a method to collect fluid, according to an embodiment.

FIG. 6 is a flow diagram of a method 600 to collect fluid, according to an embodiment. The method 600 of collecting fluid may utilize use any of the fluid collection systems disclosed herein. The method 600 may include act 610, which recites "positioning at least one opening of a fluid collection assembly adjacent to a female urethral opening." Act 610 may be followed by act 620, which recites "tensioning at least one tensioning element to switch the tensioning element from a relaxed state to a tensioned state to change a curvature of the fluid collection assembly." Act 620 may be followed by act 630, which recites "receiving one or more bodily fluids from the female urethral opening into a chamber of the fluid collection assembly."

Acts 610, 620, 630 of the method 600 are for illustrative purposes. For example, the act 610, 620, 630 of the method 600 may be performed in different orders, split into multiple acts, modified, supplemented, or combined. In an example, one or more of the acts 610, 620, 630 of the method 600 may be omitted from the method 600. Any of the acts 610, 620, or 630 may include using any of the fluid collection assemblies or systems disclosed herein.

Act 610 recites "positioning at least one opening of a fluid collection assembly adjacent to a female urethral opening." The act 610 of positioning the opening of a fluid collection assembly adjacent to a female urethral opening may include utilizing any of the fluid collection assemblies or systems disclosed herein. In some examples, act 610 may include positioning the opening of a fluid collection assembly such that the fluid permeable membrane of the female fluid collection assembly abuts or is positioned proximate to the female urethral opening. In some examples, positioning an opening of a fluid collection assembly adjacent to a female urethral opening may include positioning the opening over the female urethral opening, such as positioning a longitudinally extending opening of the fluid collection assembly over the female urethral opening.

Act 620 recites "tensioning at least one tensioning element to switch the tensioning element from a relaxed state to a tensioned state to change a curvature of the fluid collection assembly." Switching the tensioning element from the relaxed state to the tensioned state may include shaping a female fluid collection assembly to contour to the anatomy around the urethral opening. In some embodiments, switching the tensioning element from the relaxed state to the tensioned state may include forming the (e.g., a longitudinal shape of the) fluid collection assembly into an arcuate shape conforming to the perineal region of the patient. For example, switching the tensioning element from the relaxed state to the tensioned state may include forming the fluid collection assembly into an arcuate shape conforming to the vaginal and perineal region of a patient.

Act 630 recites, "receiving one or more bodily fluids from the female urethral opening into a chamber of the fluid collection assembly." In some examples, receiving bodily fluids from the female urethral opening into a chamber of the fluid collection assembly includes receiving the bodily fluids through the opening of the fluid collection assembly. Receiving bodily fluids from the female urethral opening into a chamber of the fluid collection assembly may include wicking the bodily fluids away from the opening using porous material, such as via a fluid permeable membrane and a fluid permeable support. Receiving bodily fluids from the female urethral opening into a chamber of the fluid collection assembly may include flowing the bodily fluids towards a portion of the chamber that is fluidly coupled to an inlet of a conduit in fluid communication a vacuum source. For instance, receiving bodily fluids from the female urethral opening into a chamber of the fluid collection assembly may include flowing the bodily fluids to a substantially unoccupied portion of the chamber (e.g., a fluid reservoir), to a gravimetrically low point of the chamber, etc., such as via gravity, wicking, or suction force. In some examples, wicking the bodily fluids into the chamber via the fluid permeable membrane and fluid permeable support may include wicking urine into a fluid reservoir in the fluid collection assembly.

The method 600 may include applying suction with a vacuum source effective to suction the bodily fluids from the chamber via a conduit disposed therein and fluidly coupled to the vacuum source may include using any of the vacuum sources disclosed herein. Applying suction with a vacuum source may include activating the vacuum source (e.g., suction device) in fluid communication with the inlet of the conduit in the fluid collection assembly. In some examples, activating the vacuum source in fluid communication with the inlet of the conduit in the fluid collection assembly may include supplying power to the vacuum source by one or more of flipping an on/off switch, pressing a button, plugging the vacuum source into a power outlet, putting batteries into the vacuum source, etc. In some examples, the vacuum source may include a hand operated vacuum pump and applying suction with a vacuum source may include manually operating the hand operated vacuum pump effective to suction the bodily fluids from the chamber via the conduit disposed therein that is fluidly coupled to the vacuum source.

In some examples, applying suction with a vacuum source effective to suction the bodily fluids from the chamber via a conduit disposed therein and fluidly coupled to the vacuum source may be effective to remove at least some bodily fluids (e.g., urine) from the chamber (e.g., interior region) of the fluid collection assembly. In some examples, applying suction with a vacuum source effective to suction the bodily fluids from the chamber via a conduit disposed therein and fluidly coupled to the vacuum source may be effective to transfer at least some of the bodily fluids from the chamber to a fluid storage container (e.g., a bottle or bag), such as from one or more of a reservoir, fluid permeable support, or fluid permeable membrane.

In some examples, the vacuum source (e.g., suction device) may be disposed on or within the fluid collection assembly and applying suction with the vacuum source may include activating the vacuum source. In some examples, the vacuum source may be spaced from the fluid collection assembly and applying suction with the vacuum source may include activating the vacuum source.

In some examples, applying suction with a vacuum source effective to suction the bodily fluids from the chamber via a conduit disposed therein and fluidly coupled to the vacuum source may include detecting moisture in the chamber (e.g., via one or more moisture sensors) and responsive thereto, activating the vacuum source to provide suction in the chamber. The control of the vacuum source responsive to the signals indicating that moisture or a level thereof is present in the chamber may be automatic, such as via a controller (e.g., computer programmed to perform the operation), or may merely provide an indication that a level of moisture is present that may necessitate removal of fluid from the chamber of the fluid collection assembly. In the latter case, a wearer may receive the indication (e.g., from the controller) and activate the vacuum pump manually.

In an example, the method 600 may include collecting the bodily fluids that are removed from the fluid collection assembly, such as into a fluid storage container that is spaced from the fluid collection assembly and fluidly coupled to the conduit. The fluid storage container may include any of the fluid storage containers disclosed herein.

The fluid collection assemblies disclosed herein are configured to collect one or more bodily fluids from a female urethral opening. However, it is noted that any of the concepts disclosed herein, such as tensioning elements, may be configured to collect one or more bodily fluids from a male urethral opening (e.g., penis). Examples of fluid collection assemblies that are configured to collected bodily fluids from a male urethral opening and methods of using such fluid collection assemblies are disclosed in International Application No. PCT/US20/42262 filed on Jul. 14, 2020, U.S. patent application Ser. No. 14/433,773 filed on Apr. 3, 2020, and U.S. Provisional Patent Application No. 63/047,374 filed on Jul. 2, 2020, the disclosure of each of which is incorporated herein, in its entirety, by this reference.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, or +2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

We claim:
1. A fluid collection system, comprising:
a fluid collection assembly including:
a fluid impermeable barrier defining a chamber, at least one opening, and at least one fluid outlet;
at least one porous material disposed in the chamber; and
at least one tensioning element at least partially disposed in the fluid collection assembly, the at least one tensioning element includes at least one first tensioning element on one side of the at least one opening and at least one second tensioning element on an opposite side of the at least one opening, the at least one tensioning element configured to switch from a relaxed state when the at least one tensioning element has substantially no tension force applied thereto and a tensioned state when the at least one tensioning element has a tension force applied thereto;

wherein the fluid collection assembly defines at least one channel, the at least one channel including a first channel having at least a portion of the at least one first tensioning element positioned therein, a second channel having at least a portion of the at least one second tensioning element positioned therein, and a common channel extending from the first channel and the second channel, the common channel defining an outlet of the at least one channel, a portion of the at least one tensioning element extending outwardly from the at least one channel, the at least one tensioning element moveable relative to the at least one channel, and wherein moving the portion of the at least one tensioning element that extends outwardly from the at least one channel relative to the at least one channel causes the at least one tensioning element to switch from the relaxed state to the tensioned state; and wherein switching the at least one tensioning element between the relaxed state and the tensioned state changes a curvature of at least a portion of the fluid collection assembly.

2. The fluid collection system of claim 1, wherein the fluid impermeable barrier includes at least one proximal surface defining the at least one opening and at least one distal surface opposite the proximal surface, and wherein the at least one tensioning element is positioned closer to the proximal surface than the distal surface.

3. The fluid collection system of claim 1, wherein the at least one tensioning element includes a fixed portion at or near a terminal end of the at least one tensioning element, the fixed portion fixedly attached to at least one of the fluid impermeable barrier, the at least one porous material, or a conduit disposed in the chamber.

4. The fluid collection system of claim 1, wherein the fluid impermeable barrier defines the at least one channel therein, the at least one tensioning element disposed in the at least one channel.

5. The fluid collection system of claim 4, wherein the at least one tensioning element includes at least one first tensioning element and at least one second tensioning element and the at least one channel includes at least one first channel on one side of the at least one opening and at least one second channel on an opposite side of the at least one opening, the at least one first tensioning element disposed in the at least one first channel and the at least one second tensioning element disposed in the at least one second channel.

6. The fluid collection system of claim 1, wherein the at least one tensioning element is disposed between the fluid impermeable barrier and the at least one porous material.

7. The fluid collection system of claim 1, wherein the at least one porous material includes a fluid permeable support and a fluid permeable membrane, and wherein the at least one tensioning element extends between the fluid permeable support and the fluid permeable membrane.

8. The fluid collection system of claim 1, further comprising a conduit extending through at least a portion of the chamber.

9. The fluid collection system of claim 8, wherein the conduit defines the at least one channel and the at least one tensioning element is disposed in the at least one channel.

10. The fluid collection system of claim 8, wherein the conduit defines a passageway configured to receive one or more bodily fluids, the at least one tensioning element disposed in the passageway.

11. The fluid collection system of claim 1, wherein the at least one tensioning element is disposed between the conduit and the at least one porous material.

12. The fluid collection system of claim 1, wherein the at least one tensioning element includes one or more wires.

13. The fluid collection system of claim 1, further comprising a locking mechanism configured to maintain the at least one tensioning element in the tensioned state, the locking mechanism secured or configured to be secured to a component of the fluid collection assembly.

14. The fluid collection system of claim 13, wherein the locking mechanism includes a ratchet-type device.

15. The fluid collection system of claim 14, wherein the ratchet device is configured to selectively pull the at least one tensioning element therein or release the at least one tensioning element therefrom.

16. The fluid collection system of claim 13, wherein the locking mechanism includes a slide attached to the at least one tensioning element, the slide extending at least partially around a conduit extending from the fluid outlet, the slide configured to selectively move along the conduit.

17. The fluid collection system of claim 13, wherein the locking mechanism includes tape.

18. The fluid collection system of claim 1, further comprising:
a fluid storage container; and
a vacuum source;
wherein the chamber of the fluid collection assembly, the fluid storage container, and the vacuum source are in fluid communication with each other via one or more conduits.

19. The fluid collection system of claim 1, wherein the at least one tensioning element includes at least one common tensioning element extending from the at least one first tensioning element positioned in the first channel and the at least one second tensioning element positioned in the second channel, the at least one common tensioning element positioned in the common channel; and wherein switching the at least one tensioning element between the relaxed state and the tensioned state includes pulling or at least partially releasing the at least one common tensioning element.

20. A method of using a fluid collection system, the method comprising:
positioning at least one opening of a fluid collection assembly of the fluid collection system adjacent to a female urethral opening, the fluid collection assembly including:
a fluid impermeable barrier defining a chamber, at least one opening, and at least one fluid outlet; and
at least one porous material disposed in the chamber; and
wherein the fluid collection system further comprises at least one tensioning element partially disposed in at least one channel defined by the fluid collection assembly, the at least one tensioning element includes at least one first tensioning element on one side of the at least one opening and at least one second tensioning element on an opposite side of the at least one opening, the at least one channel including a first channel having at least a portion of the at least one first tensioning element positioned therein, a second channel having at least a portion of the at least one second tensioning element positioned therein, and a common channel extending from the first channel and the second channel, the common channel defining an outlet of the at least one channel, a portion of the at least one tensioning element extending outwardly from the at least one channel; and pulling on the portion of the at least one tensioning element extending outwardly from the at least one channel to switch the tensioning element from a relaxed state to a tensioned state to change a curvature of the fluid collection assembly.

* * * * *